United States Patent
Segal et al.

(10) Patent No.: US 7,264,800 B2
(45) Date of Patent: Sep. 4, 2007

(54) METHOD AND COMPOSITION FOR INHIBITING CANCER CELL GROWTH

(75) Inventors: Donald Segal, Stouffville (CA); Jerry McElroy, Richmond Hill (CA); Heman Chao, Aurora (CA); Wah Y. Wong, Edmonton (CA); John Docherty, Richmond Hill (CA); Jodi Dickstein, Markham (CA)

(73) Assignee: Helix BioPharma Corporation, Aurora, Ontario (CA)

( * ) Notice: Subject to any disclaimer, the term of this patent is extended or adjusted under 35 U.S.C. 154(b) by 220 days.

(21) Appl. No.: 11/046,271

(22) Filed: Jan. 27, 2005

(65) Prior Publication Data

US 2005/0196391 A1    Sep. 8, 2005

Related U.S. Application Data

(63) Continuation-in-part of application No. 10/621,833, filed on Jul. 16, 2003.

(60) Provisional application No. 60/397,244, filed on Jul. 18, 2002.

(51) Int. Cl.
*A61K 38/46* (2006.01)
*C12N 9/78* (2006.01)
*C12Q 1/58* (2006.01)

(52) U.S. Cl. .................. 424/94.6; 435/12; 435/227

(58) Field of Classification Search .............. None
See application file for complete search history.

(56) References Cited

U.S. PATENT DOCUMENTS

| | | | |
|---|---|---|---|
| 4,837,380 A | 6/1989 | Deftos et al. | |
| 5,411,884 A | 5/1995 | Hellstrom et al. | |
| 5,573,934 A | 11/1996 | Hubbell et al. | |
| 5,750,496 A | 5/1998 | Forney et al. | |
| 6,126,938 A | 10/2000 | Guy et al. | |
| 6,248,330 B1 | 6/2001 | Labigne et al. | |
| 6,426,086 B1 | 7/2002 | Papahadjopoulos et al. | |
| 2003/0108966 A1 | 6/2003 | Mather | |
| 2004/0115186 A1 | 6/2004 | Segal et al. | |

FOREIGN PATENT DOCUMENTS

| | | |
|---|---|---|
| WO | WO95/22987 | 8/1995 |
| WO | WO95/31480 | 11/1995 |
| WO | WO98/37207 | 8/1998 |
| WO | WO 01/00245 | 1/2001 |

OTHER PUBLICATIONS

Bagshawe, K.D., et al., "A cytotoxic agent can be generated selectively at cancer sites," *Br. J. Cancer* 58:700-703, (1988).
Herron, J.N., et al., "Antibodies and targeting moieties: affinity measurements, conjugation chemistry and applications in immunoliposomes," *J. Controlled Release* 28(⅓):155-166, (1994).
Raghunand, N., et al., "Enhancement of chemotherapy by manipulation of tumour pH," *B. J. Cancer* 80(7):1005-1011, (1999).
Shi, G., et al., "Efficient intracellular drug and gene delivery using folate receptor-targeted pH-sensitive liposomes composed of cationic/anionic lipid combinations," *J. Controlled Release* 80(1-3):309-319, (2002).
Wampler, G.L., "Antitumor activity of acetohydroxamic acid," *Proceedings of AACR and ASCO*, Abstract 18:214, (1977).
Zimber, A., et al., "Effect of Urease Injections on Ehrlich Ascites Tumor Growth in Mice," *Proceedings of the Society for Experimental Biology and Medicine* 139(1):143-149, (1972).

*Primary Examiner*—Robert A. Wax
(74) *Attorney, Agent, or Firm*—Perkins Coie LLP; Peter J. Dehlinger

(57) ABSTRACT

Improvements in methods of treating cancer with weakly basic anti-cancer compounds are provided. In one aspect, the invention provides an improvement in a method of treating cancer cells whose extracellular environment contains 1–8 mM urea, by exposing the cells to a weakly basic anti-cancer compound which is effective in inhibiting the growth of the cells. The improvement includes (a) exposing the cells to a urease enzyme composition and, (b) by step (a), reducing the amount of anti-cancer compound required to produce a given extent of inhibition in the growth of the cells when the cells are exposed to the anti-cancer agent. Methods of potentiating the specific therapeutic activity of a weakly basic anti-cancer compound in the treatment of a given mammalian cancer which is responsive to the compound are provided as are pharmaceutical compositions for use in intravenous administration to a subject are also provided.

25 Claims, 11 Drawing Sheets

SEQUENCE LISTING

<160> NUMBER OF SEQ ID NOS: 1

<210> SEQ ID NO 1
<211> LENGTH: 840
<212> TYPE: PRT
<213> ORGANISM: Canavalia ensiformis

<400> SEQUENCE: 1

```
Met Lys Leu Ser Pro Arg Glu Val Glu Lys Leu Gly Leu His Asn Ala
 1               5                  10                  15

Gly Tyr Leu Ala Gln Lys Arg Leu Ala Arg Gly Val Arg Leu Asn Tyr
                20                  25                  30

Thr Glu Ala Val Ala Leu Ile Ala Ser Gln Ile Met Glu Tyr Ala Arg
            35                  40                  45

Asp Gly Glu Lys Thr Val Ala Gln Leu Met Cys Leu Gly Gln His Leu
        50                  55                  60

Leu Gly Arg Arg Gln Val Leu Pro Ala Val Pro His Leu Leu Asn Ala
 65                  70                  75                  80

Val Gln Val Glu Ala Thr Phe Pro Asp Gly Thr Lys Leu Val Thr Val
                 85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Lys Asp
                245                 250                 255

Ala Ser Glu Gly Phe Thr Lys Glu Asp Pro Asn Cys Pro Phe Asn Thr
            260                 265                 270
```

```
Phe Ile His Arg Lys Glu Tyr Ala Asn Lys Tyr Gly Pro Thr Thr Gly
        275                 280                 285
Asp Lys Ile Arg Leu Gly Asp Thr Asn Leu Leu Ala Glu Ile Glu Lys
    290                 295                 300
Asp Tyr Ala Leu Tyr Gly Asp Glu Cys Val Phe Gly Gly Gly Lys Val
305                 310                 315                 320
Ile Arg Asp Gly Met Gly Gln Ser Cys Gly His Pro Ala Ile Ser
                325                 330                 335
Leu Asp Thr Val Ile Thr Asn Ala Val Ile Asp Tyr Thr Gly Ile
            340                 345                 350
Ile Lys Ala Asp Ile Gly Ile Lys Asp Gly Leu Ile Ala Ser Ile Gly
        355                 360                 365
Lys Ala Gly Asn Pro Asp Ile Met Asn Gly Val Phe Ser Asn Met Ile
    370                 375                 380
Ile Gly Ala Asn Thr Glu Val Ile Ala Gly Glu Gly Leu Ile Val Thr
385                 390                 395                 400
Ala Gly Ala Ile Asp Cys His Val His Tyr Ile Cys Pro Gln Leu Val
                405                 410                 415
Tyr Glu Ala Ile Ser Ser Gly Ile Thr Thr Leu Val Gly Gly Gly Thr
            420                 425                 430
Gly Pro Ala Ala Gly Thr Arg Ala Thr Thr Cys Thr Pro Ser Pro Thr
        435                 440                 445
Gln Met Arg Leu Met Leu Gln Ser Thr Asp Asp Leu Pro Leu Asn Phe
    450                 455                 460
Gly Phe Thr Gly Lys Gly Ser Ser Ser Lys Pro Asp Glu Leu His Glu
465                 470                 475                 480
Ile Ile Lys Ala Gly Ala Met Gly Leu Lys Leu His Glu Asp Trp Gly
                485                 490                 495
Ser Thr Pro Ala Ala Ile Asp Asn Cys Leu Thr Ile Ala Glu His His
            500                 505                 510
Asp Ile Gln Ile Asn Ile His Thr Asp Thr Leu Asn Glu Ala Gly Phe
        515                 520                 525
Val Glu His Ser Ile Ala Ala Phe Lys Gly Arg Thr Ile His Thr Tyr
    530                 535                 540
His Ser Glu Gly Ala Gly Gly Gly His Ala Pro Asp Ile Ile Lys Val
545                 550                 555                 560
Cys Gly Ile Lys Asn Val Leu Pro Ser Ser Thr Asn Pro Thr Arg Pro
                565                 570                 575
Leu Thr Ser Asn Thr Ile Asp Glu His Leu Asp Met Leu Met Val Cys
            580                 585                 590
His His Leu Asp Arg Glu Ile Pro Glu Asp Leu Ala Phe Ala His Ser
        595                 600                 605
Arg Ile Arg Lys Lys Thr Ile Ala Ala Glu Asp Val Leu Asn Asp Ile
    610                 615                 620
Gly Ala Ile Ser Ile Ile Ser Ser Asp Ser Gln Ala Met Gly Arg Val
625                 630                 635                 640
Gly Glu Val Ile Ser Arg Thr Trp Gln Thr Ala Asp Lys Met Lys Ala
                645                 650                 655
Gln Thr Gly Pro Leu Lys Cys Asp Ser Ser Asp Asn Asp Asn Phe Arg
            660                 665                 670
Ile Arg Arg Tyr Ile Ala Lys Tyr Thr Ile Asn Pro Ala Ile Ala Asn
        675                 680                 685
```

```
                                    -continued

Gly Phe Ser Gln Tyr Val Gly Ser Val Glu Val Gly Lys Leu Ala Asp
    690                 695                 700

Leu Val Met Trp Lys Pro Ser Phe Phe Gly Thr Lys Pro Glu Met Val
705             710                 715                     720

Ile Lys Gly Gly Met Val Ala Trp Ala Asp Ile Gly Asp Pro Asn Ala
            725                 730                 735

Ser Ile Pro Thr Pro Glu Pro Val Lys Met Arg Pro Met Tyr Gly Thr
            740                 745             750

Leu Gly Lys Ala Gly Gly Ala Leu Ser Ile Ala Phe Val Ser Lys Ala
            755             760             765

Ala Leu Asp Gln Arg Val Asn Val Leu Tyr Gly Leu Asn Lys Arg Val
    770             775             780

Glu Ala Val Ser Asn Val Arg Lys Leu Thr Lys Leu Asp Met Lys Leu
785             790             795                     800

Asn Asp Ala Leu Pro Glu Ile Thr Val Asp Pro Glu Ser Tyr Thr Val
            805             810             815

Lys Ala Asp Gly Lys Leu Leu Cys Val Ser Glu Ala Thr Thr Val Pro
            820             825             830

Leu Ser Arg Asn Tyr Phe Leu Phe
            835         840
```

METHOD AND COMPOSITION FOR INHIBITING CANCER CELL GROWTH

CROSS-REFERENCE TO RELATED APPLICATIONS

This application is a continuation-in-part of U.S. patent application Ser. No. 10/621,833, filed Jul. 16, 2003, U.S. Publication No. 2004/0115186 A1, published Jun. 17, 2004, which claims priority to and benefit of U.S. Provisional Patent Application No. 60/397,244, filed Jul. 18, 2002. Both of these applications are incorporated herein by reference in their entirety for all purposes.

FIELD OF THE INVENTION

The present invention relates to anticancer therapeutic methods employing urease in combination with a weakly basic anti-cancer compound.

BACKGROUND OF THE INVENTION

Cancer accounts for one-fifth of the total mortality in the United States, and is the second leading cause of death. Cancer is typically characterized by the uncontrolled division of a population of cells. This uncontrolled division may involve blood cells, such as various types of lymphomas, or cells that aggregate in or are native to a particular tissue or organ, e.g., solid tumors, such as secondary or primary tumors of the breast, lung, liver, esophagus, stomach, intestines, brain, bone, or prostate.

A variety of treatment modalities have been proposed for cancer therapy. These generally include surgical resection of solid tumors, treatment with radiation, such as x-ray, chemotherapy, immune therapy, and gene therapy. The type(s) of therapy that are selected for a given cancer will depend on such factors as patient age, degree of localization of the cancer, and the type and stage of the cancer. Often the therapy will involve a combination of two or more modalities, such as x-ray therapy in combination with chemotherapy, or with immunotherapy in combination with chemotherapy.

A large number of chemotherapeutic compounds and compositions and strategies have been employed in treating cancers. Many anti-neoplastic compounds are designed to disrupt replication in rapidly dividing cells, or to inhibit a key metabolic link in actively proliferating cells. Although such approaches have met with levels of success in certain types of cancers, or cancers at certain stages, chemotherapy is generally associated with unpleasant to debilitating side effects, such as malaise, nausea, loss of appetite, alopecia, and anemia, and in the extreme, loss of immune function and/or loss of digestive activity. Further, compounds which act at the level of cell replication, either by introducing nucleotide analogs into dividing cells, or by disrupting normal replication, have the potential of introducing widespread genetic mutations in normal cells in the subject. In addition, cancer cells may develop resistance to many types of anti-cancer agents, either by limiting uptake of the agent into the cells, or by altering the metabolism of the agent within the cells.

In response to these limitations, attempts to modify chemotherapeutic agents to reduce their side effects, overcome problems of resistance, or improve their targeting to selected tumor sites have been developed. While these efforts have yielded improved therapeutic results in some cases, there remains a need to provide an improved chemotherapeutic agent and method. In particular, such an agent and method should be effective in killing or inhibiting the growth of cancer cells, should be relatively non-toxic at therapeutically effective doses, and preferably deliverable in a form that allows direct introduction into a tumor or selective targeting to tumors.

SUMMARY OF THE INVENTION

It has been discovered that the efficacy of a weakly basic anti-cancer compound can be enhanced when cancer cells, a patient or other subject is also treated with urease. That is, the amount of the weakly basic anti-cancer compound required to achieve a specified amount of growth inhibition in the presence of urease is less than in the absence of urease. Accordingly, the specific therapeutic efficacy of a given amount of anti-cancer drug in a mammalian subject can be enhanced (potentiated), by co-treating the subject with urease, typically by pretreating the subject with urease. Accordingly, improvements in a method of treating cancer cells are provided. Methods of potentiating the specific therapeutic activity of a weakly basic anti-cancer compound are provided, as are pharmaceutical compositions for use in intravenous administration of a subject.

In one aspect of the invention, improvements in a method of treating cancer cells whose extracellular environment contains 1–8 mM urea by exposing the cells to a weakly basic anti-cancer compound which is effective in inhibiting the growth of the cells is provided. In a general embodiment, the improvement includes (a) exposing the cells to a urease enzyme composition and (b) by step (a) reducing the amount of anti-cancer compound required to produce a given extent of inhibition in the growth of the cells when the cells are exposed to the anti-cancer agent.

The amount of urease to which the cells are exposed is preferably sufficient to raise the pH of the extracellular environment of the cells by at least about 0.1 pH units, typically between 0.1 to 0.5 or more pH units. The amount of anti-cancer compound required to achieve the same extent of cell-growth inhibition may be between about 2-fold and 5-fold less than in the absence of step the urease administration.

Exemplary anti-cancer agents include doxorubicin, daunorubicin, mitoxantrone, epirubicin, mitomycin, bleomycin, a vinca alkaloid, an alkylating agent, and antineoplastic purine and pyrimidine derivatives.

The urease composition may include a targeting moiety, such as an antibody directed against a tumor-specific antigen, an anti-hCG antibody, and a ligand capable of binding specifically to a cancer-cell surface receptor. The targeting moiety may be covalently attached to the urease enzyme. One exemplary targeting moiety is a single-chain antibody, such as a single-chain antibody derived from llama germline.

For use in treating a cancer in a mammalian subject, by administrating the anti-cancer compound to the subject, the urease composition administered to the subject is effective to localize at the site of the cancer into the subject. The urease composition may be administered intravenously, e.g., in an amount of between 25 and 2000 pmoles urease enzyme/kg subject body weight, at least 24 hours prior to administration of the anti-cancer compound. A urease composition administered by IV drip may include a urease inhibitor, in an amount of at least about 6 moles inhibitor/mole urease enzyme.

Alternatively, for use in treating a solid tumor, the urease composition may be administered directly in the tumor in an amount effective to raise the pH total of the extracellular fluid of the tumor, as evidenced by detectable change in a pH indicator present in the tumor extracellular fluid.

In another aspect, the invention includes a method of treating a cancer that is responsive to a selected weakly basic anti-tumor compound in mammalian subject. The method includes administering to the subject, such weakly basic anti-cancer compound, and an amount of urease sufficient to potentiate the therapeutic effect of the compound with respect to the therapeutic effect obtained in the absence of said urease administration. The urease may be administered at least 24 hours prior to administering the anti-cancer compound, allowing clearance of at least a significant portion of the urease, prior to administering the anti-cancer compound. The amount of urease administered may be effective to raise the pH of the extracellular environment of the cancer cells by at least 0.1 pH unit. The amount of urease administered may be effective, for example, to reduce the amount of said anti-cancer compound required to achieve the same extent of cell-growth inhibition by a factor of between 2 and 5.

In still another aspect, the invention includes a pharmaceutical composition for use in intravenous administration to a subject. The composition may include at least about 20 Units urease enzyme/ml; a urease inhibitor at a concentration effective to inhibit the urease enzyme, and a physiological carrier suitable for administering the composition intravenously. In one embodiment, where the enzyme has six enzymatic subunits, the molar ratio of inhibitor to enzyme is preferably at least about 6:1.

The urease enzyme may be covalently linked to a targeting agent selected from the group consisting of an antibody directed against a tumor antigen, an anti-hCG antibody, and a ligand capable of binding specifically to a cancer-cell surface receptor.

The urease inhibitor may be a hydroxamic acid derivative or other urea analog.

These and other objects and advantages of the present invention will be apparent from the description herein.

indicates the pH of urease-treated group measured after treatment. Values are means±S.D. of 4 replicates from 3 experiments.

Figure 10A:
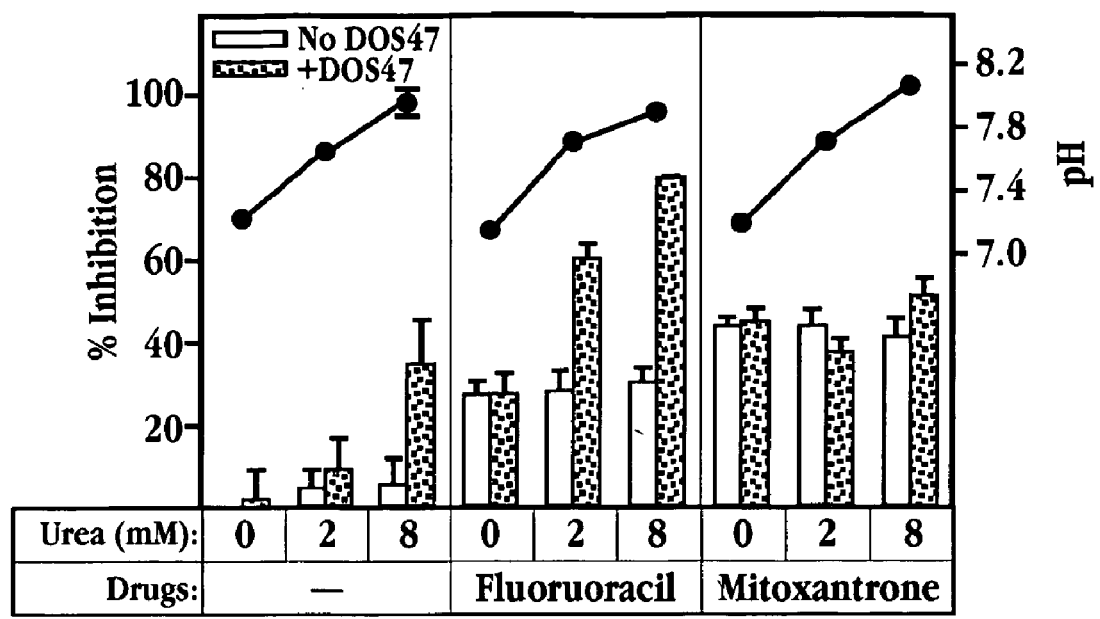
Figure 10B:
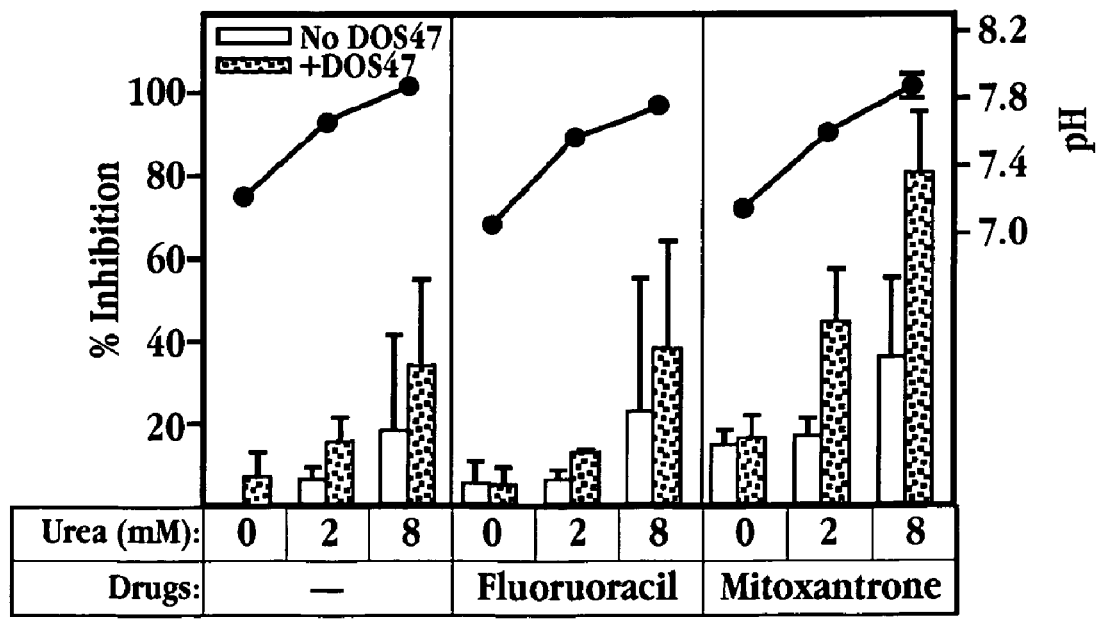

FIGS. 10A–10B are graphs showing the effects of urease on the cytotoxicity of weakly basic anticancer drugs as described in Example 11. Lung tumor A549 (A) and breast tumor MDA-MB-231 (B) were incubated in urea and treated with DOS47 (2 U/ml), and either Fluorouracil (13.3 mM) or Mitoxantrone (5 μM) at pH 6.8 overnight. The enhanced anticancer effect (solid bar) of Mitoxantrone is only observed in MDA-MB-231 but not in A549 cells. DOS47 also enhances the anticancer effects of Fluorouracil in A549 but not in MDA-MB-231. The solid circle (●) denotes the pH of DOS47 group measured after treatment. Values are means±S.D. of 4 replicates from 3 different experiments.

DETAILED DESCRIPTION OF THE INVENTION

The present invention provides improvements in selected methods of treating cancer cells, methods of potentiating the specific therapeutic activity of a weakly basic anti-cancer compound, and pharmaceutical compositions for inhibiting the growth of cancer cell, e.g., in a mammalian patient. It has been discovered that the pharmaceutical efficacy of a weakly basic anti-cancer compound can be enhanced when a mammalian subject, such as a human subject, is also treated, preferably pretreated with urease.

I. Definitions

Unless otherwise indicated, all technical and scientific terms used herein have the same meaning as they would to one skilled in the art of the present invention.

The term "urease" refers to an enzyme having the enzymatic activity of a urea amidohydrolase (E.C. 3.5.1.5), either naturally occurring or obtained by e.g., recombinant nucleic acid techniques and/or chemical synthesis. Urease also includes fusion proteins comprising the entire urease, subunits, or fragments thereof, and/or urease with amino acid substitutions, deletions or additions that preserve the urea amidohydrolase activity of the polypeptide. A truncated urease sequence as used herein is a fragment of urease that is free from a portion of the intact urease sequence beginning at either the amino or carboxy terminus of urease. Methods for isolating native urease, for synthesizing urease recombinantly, and for identifying active fragments and modified urease polypeptides are given below.

The term "cancer" is meant to refer to an abnormal cell or cells, or a mass of tissue. The growth of these cells or tissues exceeds and is uncoordinated with that of the normal tissues or cells, and persists in the same excessive manner after cessation of the stimuli which evoked the change. These neoplastic tissues or cells show a lack of structural organization and coordination relative to normal tissues or cells which may result in a mass of tissues or cells which can be either benign or malignant. As used herein, cancer includes any neoplasm. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like.

A "tumor" or "solid tumor" refers to a cohesive mass of cancer cells, including but not limited to semi-solid and solid tumors, solid tumor metastases, angiofibromas, retrolental fibroplasia, hemangiomas, and Karposi's sarcoma.

As used herein, the term "targeting moiety" refers to a molecule that is associated with urease and which is effective to promote localization of urease at cancer cells, e.g., within a solid tumor. In one general embodiment, the targeting moiety is a binding molecule covalently attached to urease and capable of binding a receptor, an oligonucleotide, an enzymatic substrate, an antigenic determinant, or other binding site present on or in the target cell or cell population. An exemplary targeting moiety is an antibody, including antibody fragments and constructs, such as a single-chain antibody, and/or an antibody derived from human germline. In another general embodiment, the targeting agent is a long-circulating particle, such as PEG-coated liposomes capable of localizing at tumor sites by extravasation, and containing encapsulated or surface bound urease.

As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

As used herein, the term "induces apoptosis" refers to the promotion of a form of programmed cell death characterized by DNA fragmentation. Apoptosis can be determined by methods known in the art. For example, kits are commercially available that detect the presence of fragmented DNA by in situ immunohistochemistry (e.g., Apoptag, available from Intergen, Purchase, N.Y.). Additionally, apoptosis can also be determined by FACS analysis, in which apoptotic cells exhibit a sub-G1 DNA content, indicating DNA fragmentation.

As used herein, an "antibody" refers to a peptide, polypeptide, or protein comprising one or more peptides or polypeptides substantially or partially encoded by at least one immunoglobulin nucleic acid molecule or immunoglobulin gene or fragment of at least one immunoglobulin molecule or immunoglobulin gene. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" chain (about 25 kD) and one "heavy" chain (about 50–70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the (Fab)'2 dimer into an Fab' monomer. The Fab' monomer is essentially a Fab with part of the hinge region (see *Fundamental Immunology*, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody", as used herein, also includes antibody fragments either produced by the modification of whole antibodies or synthesized de novo using recombinant DNA methodologies. Antibodies include single chain antibodies, including single chain Fv (sFv) antibodies in which a VH and a VL are joined together (directly or through a peptide linker) to form a continuous polypeptide. One preferred antibody is a single-chain antibody derived from a human germline.

An "antigen-binding fragment" of an antibody is a peptide or polypeptide fragment of the antibody that binds an antigen. An antigen-binding site is formed by those amino acids of the antibody that contribute to, are involved in, or affect the binding of the antigen. See Scott, T. A. and Mercer, E. I., CONCISE ENCYCLOPEDIA: BIOCHEMISTRY AND MOLECULAR BIOLOGY (de Gruyter, 3d ed. 1997) and Watson, J. D. et al., RECOMBINANT DNA (2d ed. 1992), each of which is incorporated herein by reference in its entirety for all purposes. The term "antibody fragment" also includes any synthetic or genetically engineered protein that acts like an antibody by binding to a specific antigen to form a complex.

The terms "active agent", "drug" and "pharmacologically active agent" are used interchangeably herein to refer to a chemical material or compound which, when administered to a subject induces a desired pharmacologic effect, and is intended to include a diagnostic or therapeutic agent, including radionuclides, drugs, anti-cancer agents, toxins and the like. Preferably, the term active agent includes proteins, glycoproteins, natural and synthetic peptides, alkaloids, polysaccharides, nucleic acid molecules, small molecules and the like. More preferably, the term active agent refers to proteins. An exemplary active agent is urease.

A "pH-sensitive" active agent refers to an active agent whose ability to induce a desired pharmacologic effect depends, at least in part, on the pH of the surrounding extracellular environment.

The term "clearing agent", as used herein, refers to an agent capable of binding, complexing or otherwise associating with an administered moiety, e.g., targeting moiety-ligand, targeting moiety-anti-ligand or anti-ligand alone, present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

The term "imaging agent" is meant to refer to compounds which can be detected.

The term "adjuvant" refers to a substance or agent added to a formulation or composition to aid the operation of the main ingredient.

The terms "interstitial" and "extracellular" fluid refer to the fluid lying between or bathing the cells of mammals.

The terms "subject", "individual" and "patient" are used interchangeably herein to refer to any target of the treatment. Also provided by the present invention is a method of treating tumor cells in situ, or in their normal position or location, for example, neoplastic cells of breast or prostate tumors. These in situ tumors can be located within or on a wide variety of hosts; for example, human hosts, canine hosts, feline hosts, equine hosts, bovine hosts, porcine hosts, and the like. Any host in which is found a tumor or tumor cells can be treated and is in accordance with the present invention. A subject thus includes a vertebrate, preferably a mammal, more preferably a human.

By "target cell retention time" is intended the amount of time that a urease molecule or other active agent remains at the target cell surface or within the target cell.

As used herein, the term "conjugate" encompasses chemical conjugates (covalently or non-covalently bound), fusion proteins and the like.

The terms "protein", "polypeptide" or "peptide", as used herein, refer interchangeably to a biopolymer composed of amino acid or amino acid analog subunits, typically some or all of the 20 common L-amino acids found in biological proteins, linked by peptide intersubunit linkages, or other intersubunit linkages. The protein has a primary structure represented by its subunit sequence, and may have secondary helical or pleat structures, as well as overall three-dimensional structure. Although "protein" commonly refers to a relatively large polypeptide, e.g., containing 100 or more amino acids, and "peptide" to smaller polypeptides, the terms are used interchangeably herein. That is, the term "protein" may refer to a larger polypeptide, as well as to a smaller peptide, and vice versa.

A "modulator of urease" is either an inhibitor of urease or an enhancer of urease.

An "inhibitor of urease" comprises a molecule or group of molecules that interferes with: (1) the expression, modification, regulation, activation or degradation of urease; or (2) one or more of the normal functions of urease. The normal functions of urease include the hydrolysis of urea, leading to the production of carbamate and ammonia. An inhibitor "acts directly on urease" when the inhibitor binds to urease via electrostatic or chemical interactions. Such interactions may or may not be mediated by other molecules. An inhibitor acts "indirectly on urease" when its most immediate effect is on a molecule other than urease which influences the expression, activation or functioning of urease.

An "enhancer of urease" comprises a molecule or group of molecules that enhances: (1) the expression, modification, regulation or activation of urease; or (2) one or more of the normal functions of urease. An enhancer acts "indirectly on urease" when its most immediate effect is on a molecule other than urease which influences the expression, activation or functioning of urease.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

A "pharmaceutically acceptable formulation" comprises a formulation that is suitable for administering the active agent (e.g., urease or urease modulator) in a manner that gives the desired results and does not also produce adverse side effects sufficient to convince a physician that the potential harm to a patient is greater than the potential benefit to that patient. The basic ingredient for an injectable formulation is typically a water vehicle. Aqueous vehicles that are useful include sodium chloride (NaCl) solution, Ringer's solution, NaCl/dextrose solution, and the like. Water-miscible vehicles are also useful to effect full solubility of the active agent. Antimicrobial agents, buffers and antioxidants may be useful, depending on the need. Similarly, a "pharmaceutically acceptable" salt or a "pharmaceutically acceptable" derivative of a compound, as provided herein, is a salt or other derivative which is not biologically or otherwise undesirable.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "small molecule" includes a compound or molecular complex, either synthetic, naturally derived, or partially synthetic, and which preferably has a molecular weight of less than 5,000 Daltons. More preferably, a small molecule has a molecular weight of between 100 and 1,500 Daltons.

As used herein, "effective amount" or "pharmaceutically effective amount" of an active agent refers to an amount sufficient to derive a measurable change in a physiological parameter of the target cell or subject and/or to provide or modulate active agent expression or activity through administration of one or more of the pharmaceutical dosage units. Such effective amount may vary from person to person depending on their condition, height, weight, age, and/or health, the mode of administering the active agent (e.g., urease or urease modulator), the particular active agent administered, and other factors. As a result, it may be useful to empirically determine an effective amount for a particular patient under a particular set of circumstances.

The term "specific therapeutic efficacy" of an active agent as used herein means the amount of an active agent which is required to achieve a specified amount or degree of therapeutic efficacy, e.g., by inhibition of cancer cell growth or killing of cancer cells or shrinkage of tumor size.

All publications and patents cited herein are expressly incorporated herein by reference for the purpose of describing and disclosing compositions and methodologies which might be used in connection with the invention.

II. Compositions Used in the Treatment Methods

This section considers the urease composition and anticancer compounds used in practicing the method of the invention.

A. Urease Composition

As noted above, the urease composition includes urease enzyme and may additional include a targeting agent associated with the enzyme for localizing urease at a target, e.g., tumor site. The urease may be of any origin, including, e.g., bacteria, plants, fungi and viruses. A number of studies have provided detailed information about the genetics of ureases from a variety of evolutionarily diverse bacteria, plants, fungi and viruses (Mobley, H. L. T. et al. (1995) *Microbiol. Rev.* 59: 451–480; *Eur J. Biochem.*, 175, 151–165 (1988); Labigne, A. (1990) International publication No. WO 90/04030; Clayton, C. L. et al. (1990) *Nucleic Acid Res.* 18, 362; and U.S. Pat. Nos. 6,248,330 and 5,298,399, each of which is incorporated herein by reference). Of particular interest is urease that is found in plants (Sirko, A. and Brodzik, R. (2000) *Acta Biochim Pol* 47(4): 1189–95). One exemplary plant urease is jack bean urease, which is described in Examples 2–3. An exemplary amino acid sequence of jack bean urease is represented by SEQ ID NO: 1 below.

Useful urease sequences may be identified in public databases, e.g., Entrez (www.ncbi.nlm.nih.gov/Entrez). Additionally, primers that are useful for amplifying ureases from a wide variety of organisms may be utilized by employing the CODEHOP (COnsensus-DEgenerate Hybrid Oligonucleotide Primer) as described in Rose, et al. (1998) *Nucl. Acids Res.* 26:1628.

The urease may contact the tumor cells, be positioned in the extracellular environment or interstitial fluid surrounding the tumor cells, or be expressed within the cancer cells or cells nearby the cancer cells. While not wishing to be bound by any specific molecular mechanisms underlying the successful inhibition of growth of cancer cells by urease, the urease compound acts to raise the pH of interstitial fluid in which the cancer cells are bathed, by conversion of urea, which is typically present in an amount between about 1–8 mM, typically about 1.5–5 mM urea, in interstitial or extracellular fluid, to ammonia and carbamate (FIGS. 1A–1D). The environment around a cancer cell is typically acidic, e.g., about 6.8. (Webb, S. D., et al. (2001) *Novartis Found Symp* 240:169–81). Thus, by raising the pH of the extracellular environment in this manner, growth of the cancer cell is inhibited. Accordingly, addition of the active agent in certain embodiments of the invention causes the pH of the interstitial fluid to be raised by about 0.1 pH unit, e.g., 0.1–0.5 pH units or greater.

Thus, active agents of the urease composition include the naturally occurring forms of urease as well as functionally active variants thereof. The nature of these active variants is more fully described in the above cited, co-owned U.S. patent application (publication No. 2004/0115186 A1, also referred to herein as the '186 application), which is incorporated herein by reference.

A1 Targeting Agent

The urease composition employed in the method of the invention may include a chemical entity associated with urease to enhance its localization at target cancer cells. A variety of associated chemical entities are contemplated and are described in the above-cited, co-owned '186 application.

One preferred chemical entity is covalently bound targeting agent, also as detailed in the '186 application. As described there, targeting moieties useful in localizing the urease composition to a target site include antibodies and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also contemplated targeting moieties.

Oligonucleotides, e.g., antisense oligonucleotides that are complementary to a portion of a target cell nucleic acid, may be used as targeting moieties in the present invention. Targeting moieties may also be oligonucleotides that bind to a target cell surface. Analogs of the above-listed targeting moieties that retain the ability to bind to a defined target cell population may also be used as targeting moieties.

Preferred targeting moieties of the present invention are antibodies, peptides, oligonucleotides or the like, that are reactive with an antigen on the surface of a target cell. Both polyclonal and monoclonal antibodies which are either available commercially or described in the literature may be employed. The antibodies may be whole antibodies or fragments thereof. Monoclonal antibodies and fragments may be produced in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. In one embodiment, the antibody is a single-chain antibody derived form a mammalian germline, e.g., llama germline. Methods for preparing conjugate composition between urease and such targeting agents are detailed in the above-cited '186 application.

A2. Entrapped Active Agents

In certain embodiments, the invention contemplates the use of vesicles such as liposomes and/or nanocapsules as chemical entities for the delivery of an active agent or active agents, e.g., urease to cancer cells. Such formulations may be preferred for the introduction of pharmaceutically-acceptable formulations of the polypeptides, pharmaceuticals, and/or antibodies disclosed herein. The formation and use of liposomes is generally known to those of skill in the art. (See, e.g., Backer, M. V., et al. (2002) *Bioconjug Chem* 13(3):462–7). In a preferred embodiment, the disclosed composition may be entrapped in a liposome. Particle-entrapped urease compositions suitable for use in the invention are detailed in the above-cited '186 application.

A3. Urease Inhibitor or Activator

Active agent modulators are also contemplated as associated chemical entities by the instant invention. A preferred active agent modulator is a urease modulator. A "urease modulator" is either an inhibitor of urease or an enhancer of urease. The modulator in the compositions (e.g., pharmaceutical compositions) accordingly may be selected from among all or portions of urease polynucleotide sequences, urease antisense molecules, urease polypeptides, protein, peptide, or organic modulators of urease bioactivity, such as inhibitors, antagonists (including antibodies) or agonists. Preferably, the modulator is active in treating a medical condition that is mediated by, or ameliorated by, urease expression or urease activity.

An "inhibitor of urease" comprises a molecule or group of molecules that interferes with: (1) the expression, modification, regulation, activation or degradation of urease: or (2) one or more of the normal functions of urease, including the hydrolysis of urea leading to the production of carbamate and ammonia. An inhibitor "acts directly on urease" when the inhibitor binds to urease via electrostatic or chemical interactions. Such interactions may or may not be mediated by other molecules. Where the inhibitor acts directly on urease, such as where the inhibitor is a reversible inhibitor, a preferred inhibitor will dissociate from urease when urease is diluted in the blood circulatory system and/or when it reaches its cellular target. An inhibitor acts "indirectly on urease" when its most immediate effect is on a molecule other than urease which influences the expression, activation or functioning of urease.

Urease inhibitors, which serve to slow the conversion of urea to ammonium ions, include but are not limited to hydroxamic acid derivatives and other urea analogs, (e.g., acetohydroxamic acid), phosphoramide derivatives (e.g., flurofamide), phosphates, thiols (e.g., 2-mercaptoethanol etc.), boric acid, halogen compounds (e.g., fluorides etc.), and cassia bark extract. Additional urease inhibitors are known to those of skill in the art and are described in U.S. Pat. No. 4,824,783 (Apr. 25, 1989) which is incorporated herein by reference. The effect of a urease inhibitor, such as acetohydroxamic acid (AHA), on urease cytotoxicity in tumor cells in culture is seen in Example 9. In this example, it is seen that tumor cells are protected from urease cytotoxicity in the presence of a urease inhibitor. Therefore, possible toxicity to the patient caused by local high concentrations of urease can be mitigated through the use of a urease inhibitor, such as AHA, especially when the enzyme is applied in bolus form. e.g., by IV drip, to reduce localized toxicity effects. AHA is commercially available under the trade name Lithostat® and has been approved for human use.

An "enhancer of urease" comprises a molecule or group of molecules that enhances: (1) the expression, modification, regulation or activation of urease; or (2) one or more of the normal functions of urease. An enhancer "acts directly on urease" when the enhancer binds to urease via electrostatic or chemical interactions. Such interactions may or may not be mediated by other molecules. An enhancer acts "indirectly on urease" when its most immediate effect is on a molecule other than urease which influences the expression, activation or functioning of urease.

In accordance with one aspect of the invention, a urease composition includes a urease and an inhibitor, e.g., AHA, at a mole ratio of urease:inhibitor sufficient to bind to all of the urease active sites, e.g., all six active sites of a normal bacterial urease. This composition therefore contains inhibitor and urease at a mole ratio of 6:1 or greater, e.g., 10:1 inhibitor:urease. At the relatively high concentration of urease employed injected or infused into a patient, the majority of the inhibitor will be in bound form, thus inhibiting strongly inhibiting the activity of the enzyme and reducing enzyme toxicity at and near the site of administration. As the urease is carried toward the target site, e.g., in the bloodstream, it will become more dilute, shifting the kinetics of inhibitor binding toward its unbound form, and thereby releasing the inhibitory effect on the enzyme with migration toward the target.

A pharmaceutical composition that includes urease enzyme and a urease inhibitor, such as the inhibitors previously described herein, may include at least about 1000 Units urease, where the concentration of enzyme and inhibitor will be determined by the solution volume to be infused or injected. Thus, a composition injected in a total volume of 10 ml will have a urease concentration 1/100 of that intended slow IV infusion in a 1 liter volume. The concentration of urease in the composition, when in aqueous form, is preferably at least about 20 Units/ml.

B. Weakly Basic Anti-Cancer Agents

The method of the invention is based on the discovery herein that exposing cancer cells to urease, i.e., by localizing urease at the site of cancer in a mammalian subject, is effective in potentiating the anti-cancer effect of a weakly basic anti-cancer compound that is effective against that cancer. This effect may be exploited, in accordance with the invention, to achieve a comparable therapeutic effect at a reduced compound dose, e.g., a dose that is 2–5 fold lower than that otherwise required, and/or to achieve a superior therapeutic effect at the same or reduced dose.

Weakly basic anti-cancer compounds include any anti-cancer compound having one or more ionizable primary or secondary amine groups, and whose uptake into cancer cells may be affected by the intracellular/lower extracellular pH gradient in the extracellular environment of the cells. Exemplary weakly basic anti-cancer compounds include doxorubicin, daunorubicin, mitoxantrone, epirubicin, mitomycin, bleomycin, vinca alkaloids, such as vinblastine and vincristine, alkylating agents, such as cyclophosphamide and mechlorethamine hydrochloride, antineoplastic purine derivatives, including cladribine, fludarabine, 6-mercaptopurine, thiamiprine, thioguanine or tiazofurin, and antineoplastic pyrimidine derivatives, including ancitabine, azacitidine, 6-azauridine, capecitabine, carmofur, cytarabine, decitabine, doxifluridine, emitefur, enocitabine, floxuridine, gemcitabine or tegafur.

Although the invention is directed potentiating the anti-cancer effect of weakly basic anti-cancer drugs, urease also appears to potentiate the anti-cancer effect of other anti-cancer drugs, such as fluorouracil (see examples below). The potentiating effect may be related to a shift in extracellular or intracellular pH caused by urease, or may involve one or more other mechanisms related to the anti-cancer effects of urease alone, detailed in the above-cited '186 application. Thus, in a more general aspect, the present invention contemplates potentiating the anti-cancer activity of any anti-cancer compound, such as fluorouracil, whose activity is enhanced by the presence, in the extracellular fluid of target cancer cells, of an amount of urease effective to raise the pH of such extracellular fluid.

C. pH-Sensitive Imaging Agents

Imaging agents may be included in the composition or in additional compositions, as detailed in the above-cited '168 application. Of particular interest for the present invention are pH sensitive imaging agents that can be used to detect and monitor changes in the local pH environment of cancer cells, e.g., the extracellular matrix of a solid tumor. Thus, for example, in practicing the present invention, it may be advantageous, in determining a suitable initial dose of the urease composition, to monitor the subject tumor site for urease-induced pH changes. Typically, an increase in pH of at least 0.1 pH units is desired, with changes of between 0.1 to 0.5 pH units or greater being typical.

Both luminescent cyclen-based lanthanide chelates and those primarily yielding magnetic resonance signatures have been shown to be sensitive to changes in pH. Luminescent probes used for sensing pH changes typically detect changes in the fluorescence lifetime of the lanthanide ion as a function of pH. Analogously, magnetic resonance contrast agents which modulate the water proton relaxivity via changes in pH are useful in the instant invention. In both cases, by changing the pH in a given system, one can envision agents with enhanced contrast.

Accordingly, a pH sensitive contrast agent is utilized at or near the cancer cell. The cancer cell or cells are also exposed to a urease composition containing urease enzyme to cause a change in pH at or near the cancer cell. In this way, a change in pH causes the nuclear magnetic resonance relaxation properties of water protons or other nuclei in the aqueous medium to be changed in a manner that is reflective of pH. Examples of pH sensitive contrast agents that may be utilized include those agents that contain a lanthanide metal, such as Ce, Pr, Nd, Sm, Eu, Gd, Db, Dy, Ho, Er, Tm, Yb, and the like, or another paramagnetic element, such as Fe, Mn, or the like. Specific contrast agents that may be utilized include GdDOTA4AmP(5-) which is described in *Magn Reson Med.* 2003 February;49(2):249–57, and Fe(III)meso-tetra(4-sulfonatophenyl)porphine (Fe-TPPS4) as described in Helpern et al. (1987) *Magnetic Resonance in Medicine* 5:302–305 and U.S. Pat. No. 6,307,372, which is incorporated herein by reference. In addition, Gd based with poly-ion, as described in Mikawa et al. *Acad. Radiol* (2002) 9(suppl 1):S109–S1111, may be used in the invention.

As another alternative, a shift reagent may be provided in the aqueous medium surrounding the cancer cell. The shift reagent is configured such that a change in pH affects the chemical shift properties of the water protons or other nuclei in a manner that is reflective of pH. The change in chemical shift properties may then be measured using nuclear magnetic resonance to determine whether the active agent is biologically active. Examplary shift reagents that may be used include those containing a lanthanide metal, such as Ce, Pr, Nd, Sm, Eu, Gd, Db, Dy, Ho, Er, Tm, or Yb, or another paramagnetic element. Examples of specific shift reagents that may be utilized include Tm(DOTP) (5-), the thulium (III) complex of 1,4,7,10-tetraazacylododecane-N, N',N",N'''-tetra(methylenephospate). Dy(PPP) (2)(7)-dysprosium tripolyphosphate, and the like.

In one embodiment of the invention, a dual-contrast-agent strategy using two gadolinium agents, such as the pH-insensitive GdDOTP(5-) and the pH-sensitive GdDOTA-4AmP(5-), may be utilized to generate pH maps by MRI, as described in *Magn Reson Med* (2003) February; 49(2): 249–57. Preferred agents for use with PET scan include 13N and fluorodeoxyglucose (FDG).

III. Method of Potentiating a Weakly Basic Anticancer Compound

The present invention provides a method of potentiating the specific therapeutic activity of a weakly basic anti-cancer compound in the treatment of a mammalian cancer that is responsive to that compound. In one general embodiment, a method includes administering to the subject an amount of a urease composition which, when given in the presence of urease, e.g., either by co-administration of urease and the compound or following administration or urease, is effective to reduce the amount of the compound needed to achieve a selected anti-cancer effect, e.g., tumor shrinkage.

The degree of potentiation achievable with the invention will depend upon a number of factors that can be readily assessed during treatment, and the compound dosaging can be adjusted accordingly during treatment. To the extent the potentiation of weakly basic anti-neoplastic agents is attributable to a shift in the external/internal pH gradient of the cancer cells, the extent of potentiation will depend on the extent to which the shift in gradient enhances drug uptake.

For example, compounds that are readily taken up with ambient gradients may show less potentiation than those whose uptake is strongly affected by a pH change in the range 6.8 to about 7.2 or higher. Similarly, where the cancer cells have developed drug resistance that relies on pumping drug out of the cells, the urease potentiation effect may be less pronounced. That is, the degree or extent of potentiation achieved will depend on a variety of factors, including the pK or $pK_a$s of the drug amine group(s); the presence or absence of drug-resistance mechanisms in the cancer cells, including those related to drug transport; the presence or absence of drug-specific transport mechanisms in the cancer cells; and the solubility of the drug in a lipid membrane. In a typical method, the extent of potentiation is between 2 and 5 fold; that is, the amount of compound needed to produce a given anti-cancer effect is 2- to 5-fold lower when the cells are pretreated by urease.

In selecting a weakly basic anti-cancer drug for treating a particular cancer, the physician will typically select a compound that has been routinely used or has demonstrated effectiveness against the particular type of cancer being treated. Table 2 below provides a partial list of weakly basic anti-cancer drugs that have been shown to be effective against a variety of human cancer types, as indicated in the table.

TABLE 2

Weakly Basic Agents Used in Cancer Treatment Which Can be Potentiated by Increased Extracellular pH

| Compound | Application | Comments |
| --- | --- | --- |
| Doxorubicin (Adriamycin ®, Rubex ®, Doxil ®, Caelyx ®, Myocet ®) | Breast Cancer<br>Ovarian Cancer<br>Lung Cancer<br>Bladder Cancer<br>Gastric Cancer<br>Thyroid Cancer | An anthracycline antibiotic from the fungus Strep. It interferes with DNA production in the cell |
| Daunomycin (Cerubidine ®) | Acute Myelogenous Leukemia<br>Acute Lymphocytic Leukemia | An anthracycline antibiotic. It interferes with DNA production in the cell |
| Epirubicin (Ellence ®) | Breast Cancer | An anthracycline antibiotic. It interferes with DNA production in the cell |
| Vinblastine (Velban ®, Velbe ®) | Breast Cancer<br>Hodgkin's Disease<br>Kaposi's Sarcoma<br>Testicular Cancer | A vinca alkaloid. It inhibits cell division during early mitosis |
| Vincristine (Oncovin ®, Vincasar PFS ®, Vincrex ®) | Acute Leukemia<br>Rhabdoyosarcoma<br>Neuroblastoma<br>Lymphorecticular Neoplasms | A vinca alkaloid. It inhibits cell division during early mitosis |
| Mitoxantrone (Novantrone ®) | Prostate Cancer<br>Acute Nonlymphocytic Leukemia | An intercalating agent that interacts with DNA and blocks DNA synthesis |
| Bleomycin (Blenoxane ®) | Squamous Cell Carcinomas<br>Hodgkin's Disease<br>Non-Hodgkin's Lymphoma<br>Testicular Cancer | A mixture of cytotoxic antibiotics, thought to inhibit DNA synthesis and, to a lesser degree, RNA and protein synthesis |
| Mitomycin (Mutamycin ®) | Gastric Cancer<br>Anal Cancer<br>Colon Cancer<br>Breast Cancer<br>Non-Small Cell Lung Cancer<br>Head and Neck Cancer<br>Small Bladder Papillomas<br>Pancreatic Cancer<br>Cervical Cancer | An alkylating agent. It is thought to inhibit cell growth by causing inter/intrastrand crosslinkages in DNA, thereby causing miscoding, breakage and replication failures |
| Mechlorethamine Hydrochloride (Mustargon ®) | Hodgkin's Disease | An alkylating agent. It is thought to inhibit cell growth by causing inter/intra strand crosslinkages in DNA, thereby causing miscoding, breakage and replication failures |

In the treatment method, the subject is typically pretreated with a selected dose of the urease composition. Where a urease composition is injected directly into a tumor, an exemplary dose is 0.1 to 1,000 international units urease activity per $mm^3$ tumor. For example, and assuming a relatively uniform distribution of the urease in the tumor is achieved, a dose of between 0.5 and 5 international units may be suitable. The placement of the injection needle may be guided by conventional image guidance techniques, e.g., fluoroscopy, so that the physician can view the position of the needle with respect to the target tissue. Such guidance tools can include ultrasound, fluoroscopy, CT, MRI, pr PET scan.

The effectiveness or distribution of the administered urease dose may be monitored, during or after direct injection of urease into the tumor, by monitoring the tumor tissue by a tool capable of detecting changes in pH within the cancerous tissue region of the subject. Such tools may include a pH probe that can be inserted directly into the tumor, or a visualization tool, such as magnetic resonance imaging (MRI), computerized tomography (CT), or fluoroscopy. MRI interrogation may be carried out in the absence of additional imaging agents, based simply on differences in magnetic properties of tissue as a function of pH. CT or fluoroscopic imaging may require an additional pH-sensitive imaging agent whose opacity is affected by the pH of the tissue medium. Such agents are well known to those of skill in the art.

Before any urease injection, the tumor tissue can be visualized by its lower pH relative to surrounding normal tissue. Thus, the normal tissue may have a normal pH of about 7.2, whereas the tumor tissue may be 0.1 to 0.4 or more pH units lower. That is, before any urease is injected, the extent of tumor tissue can be defined by its lower pH. Following urease administration, the pH of the tumor region having urease will begin to rise, and can be identified by comparing the resulting images with the earlier pre-dosing images.

By interrogating the tissue in this manner, the degree of change in pH and extent of tissue affected may be monitored. Based on this interrogation, the physician may administer additional urease composition to the site, and/or may administer composition at additional areas within the tumor site. This procedure may be repeated until a desired degree of pH changes, e.g., 0.2 to 0.4 pH units, has been achieved over the entire region of solid tumor.

Where the urease is administered parenterally by a method other than direct injection, e.g., by IV drip, an exemplary dose of the urease is 100–100,000 international units urease activity/kg subject body weight, or alternatively, between about 25–2000 pmoles, preferably 25–500 pmolesurease/kg subject body weight. As noted herein, the urease composition in this method preferably includes a targeting agent for targeting urease to the cancer cells, e.g., site of solid tumor, or for sequestering urease, e.g., in liposomal form, selectively at the tumor site. The composition described above containing urease in combination with stoichiometric amounts of an inhibitor is advantageous in intravenous administration for the reasons discussed above. As above, imaging techniques that are sensitive to changes in tissue pH, may be used to monitor urease dosing.

Where the urease composition is given by IV injection or drip, the urease is typically allowed to clear from the body for a period of at least 24 hours prior to administration of the anti-cancer compound. The rate of clearance can be accelerated, if desired, by administering a clearing agent, such as an anti-urease antibody, that facilitates clearance by non-renal clearance mechanisms. Such methods are well known.

Once an adequate dose of the urease composition has been administered and localized at the target site, and preferably after a period that allows for clearance of a significant portion of the circulating urease, the anti-cancer compound is administered by conventional dosing methods, e.g., oral administration or IV drip. According to an important feature of the invention, the urease localized at the cancer site potentiates the anti-cancer drug, allowing a significantly reduced dose of the compound to be administered, and/or a greater therapeutic efficacy to be achieved at the same or reduced dose. As noted above, the reduction in dose of anti-cancer compound is typically 2- to 5-fold over that in the absence of urease, and these values can be used as a guide to dosing in the method. Thus, the physician may start with a dose that is ½ that of conventional dosing, and if a good therapeutic result is achieved, the dose could be reduced further until a lowest effective dose is reached. Preferably, the dose administered will be the highest dose compatible with patient comfort and lack of undesired side effects, such as nausea, alopecia, malaise, and loss of a significant portion of white blood cells, allowing effective cancer therapy with substantially reduced discomfort and long-term risk to the patient.

In a typical anti-cancer treatment, the anti-cancer drug is administered at twice or three-times weekly dosing over a 2–4 week period, followed by a recovery and observation period of one to several months. In the present invention, this regimen may be supplemented by urease administration preceding each dosing, or preceding each dosing period, e.g., once a week or once every other week during the period of compound treatment. The frequency of urease administration may be assessed during treatment by periodic assessment of localized pH levels at the cancer site, using the above pH monitoring tools.

During the course of treatment, the size and shape of a tumor may be monitored by diagnostic tools, such as those described above. In particular, the subject can be interrogated with a diagnostic tool capable of detecting changes in extracellular pH in a subject's tissue, as described above. The diagnostic tool is preferably a pH-sensitive diagnostic agent, such as an imaging, contrast or shift reagent, as described in Section II, above, capable of localizing in the tumor that may be administered prior to, following or concurrently with the active agent. A tissue region is identified within the subject that shows an elevation in extracellular pH following the administration. Any tool capable of identifying the diagnostic agent may be used to detect the agent, such as MRI, PET scan, and the like, as described above.

In one embodiment, the method includes administering urease to the subject employed in an anti-cancer therapy, and the identification is used for detecting the localization of urease in a solid tumor. The identifying may be used for monitoring the change in size and shape of the tumor in response to urease administration.

In one embodiment employing PET scan, the subject is administered 13N-labelled ammonia. The patient is then administered urease in an amount effective to reach the tumor site. The urease hydrolyzes urea to produce non-labelled ammonia. Over time, the labelled ammonia is diluted or displaced, causing a gradual clearing on the scan.

In another embodiment employing PET scan, the subject is administered 13N-labelled urea. The patient is then administered urease in an amount effective to reach the tumor site. The urease hydrolyzes the labelled urea to produce labelled ammonia, which could be detected on the scan.

From the foregoing, it can be seen how various objects and features of the invention are met. The invention provides an effective and relatively simple method for potentiating the therapeutic effect of a large class of anti-cancer compounds. This potentiation allows a comparable or superior anti-cancer effect to be achieved at a lower dose of compound, thus reducing patient discomfort, health risks to the patient, and improving patient compliance and prospects for recovery. The dosing and localization of urease can be readily monitored, according to localized pH changes, and these same changes can be used to monitor the efficacy of the treatment method, and to monitor the urease dosing administered.

The following examples further illustrate the invention described herein and are in no way intended to limit the scope of the invention.

A. EXAMPLE 1

A1. Peptide Synthesis

Peptides were prepared by solid-phase synthesis methodology using conventional N-t-butyloxycarbonyl (t-Boc) chemistry. Peptides were cleaved from the resin by reaction with hydrogen fluoride (20 ml/g resin) containing 10% anisole and 2% 1,2-ethanedithiol for 1.5 h at 4° C. Crude peptides were washed with cold ether, and extracted from the resin with glacial acetic acid and freeze-dried. Synthetic peptide was purified by reversed-phase HPLC on a Zorbax semi-preparative C-8 column (250×10 mm I.D., 6.5-µm particle size, 300-Å pore size) with a linear AB gradient (ranging from 0.2 to 1.0% B/min) at a flow rate of 2 ml/min, where solvent A is aqueous 0.05% trifluoroacetic acid (TFA) and solvent B is 0.05% TFA in acetonitrile. Homogeneity of the purified peptides was verified by analytical reversed phased-HPLC, amino acid analysis and MALDI mass spectrometry.

A2. Affinity Purification of Urease

The affinity column was prepared by reacting hydroxyurea to epoxy-activated Sepharose 6B (Amersham Biosciences). Remaining active groups were blocked using 1 M ethanolamine.

Figure 1A:
FIGS. 1A–1D illustrate the steps of the urease reaction. Urea is cleaved by urease to produce one molecule of ammonia and one of carbamate (A). Carbamate spontaneously decomposes to ammonia and carbonic acid (B). The carbonic acid equilibrates in water (C), as do the two molecules of ammonia, which become protonated to yield ammonium and hydroxide ions (D). The reaction results in a rise in the pH of the reaction environment.
Figure 1B:
Figure 1C:
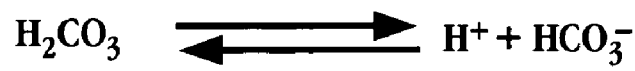
Figure 1D:
Figure 2:
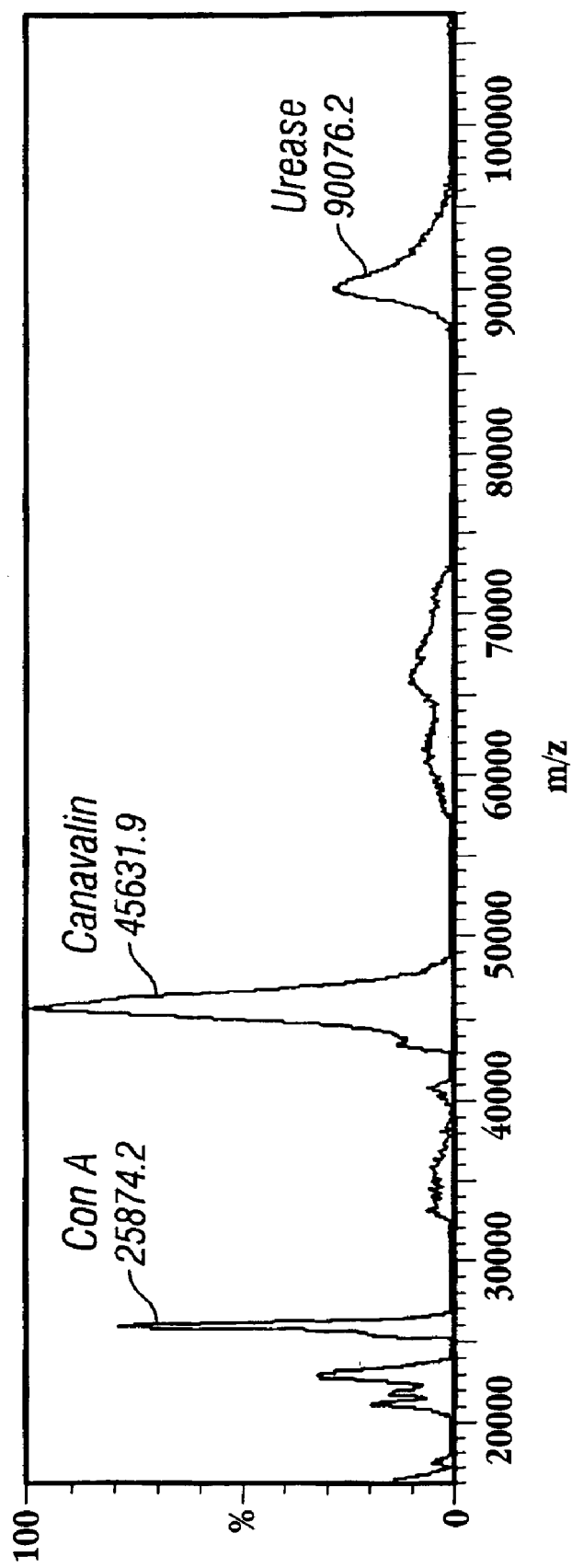
FIG. 2 shows the mass spectrometry profile of a crude sample containing urease prepared in accordance with one embodiment of the invention.
Figure 3A:
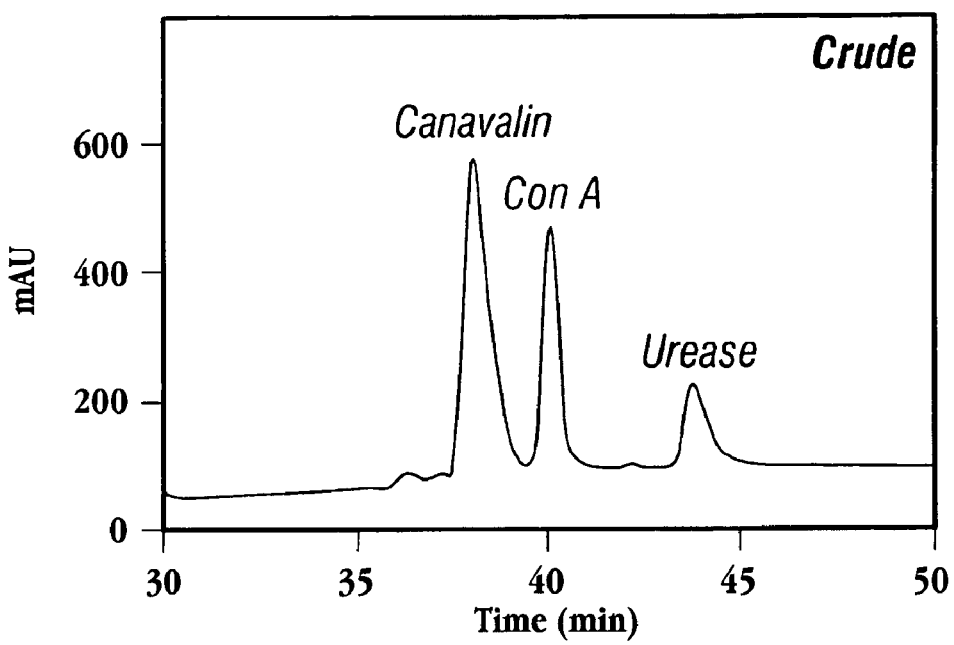
FIG. 3 illustrates the affinity purification profiles of urease during various stages of the purification process, in accordance with another embodiment of the invention.
Figure 3B:
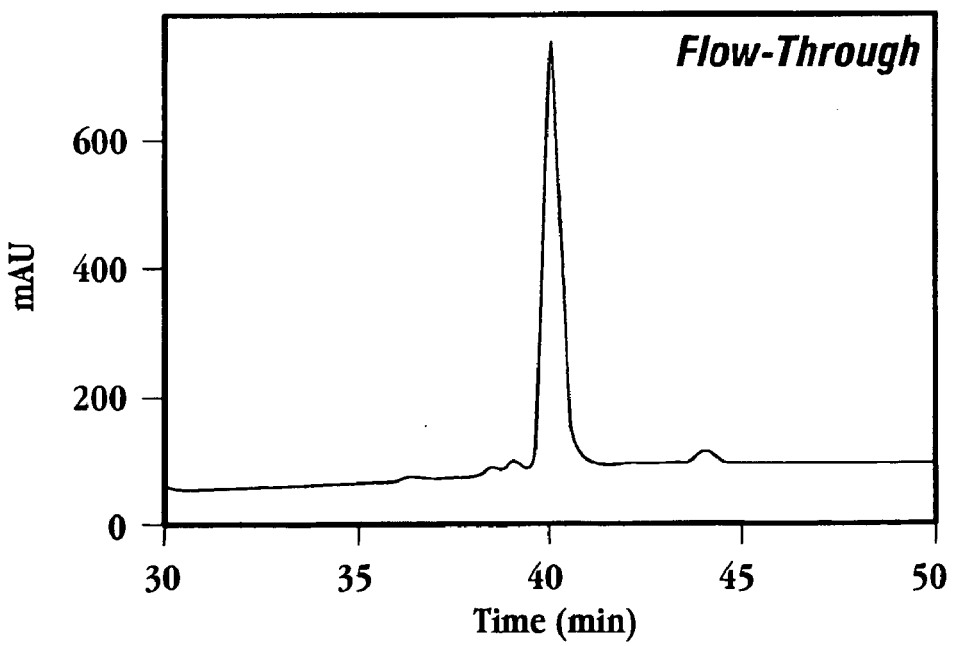
Figure 3C:
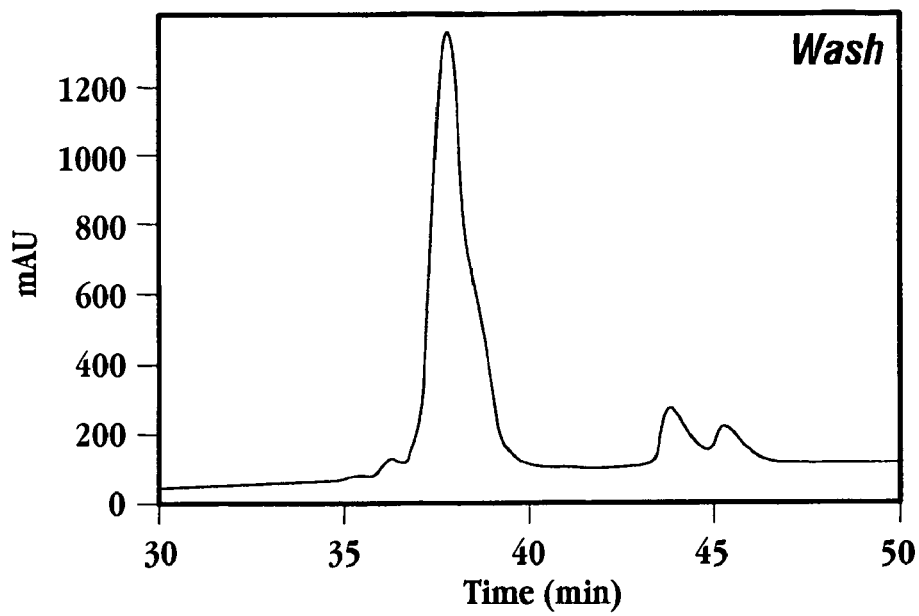
Figure 3D:
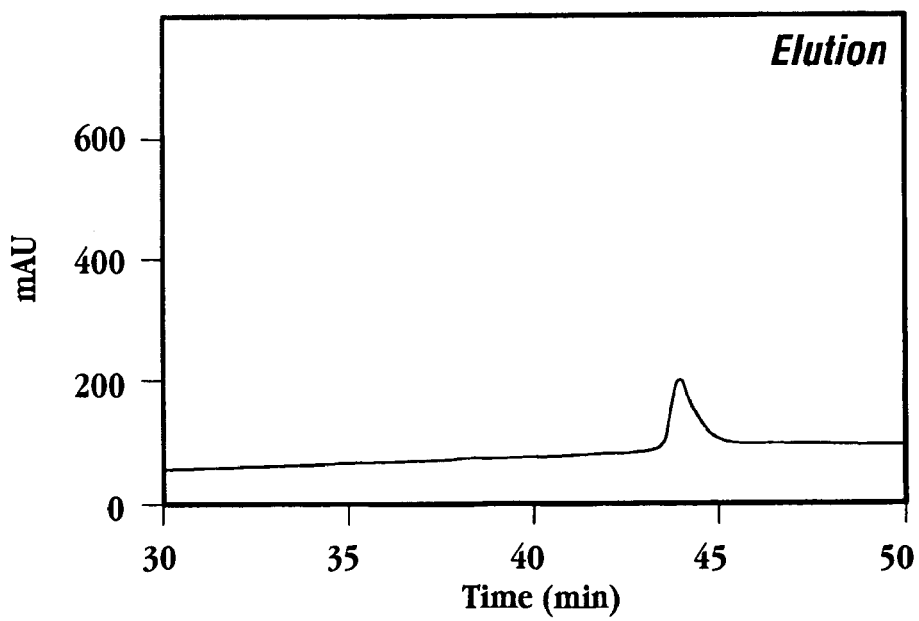

Purification was performed as follows. The column was equilibrated with PEB (0.02 M phosphate, 1 mM EDTA, 1 mM β-mercaptoethanol, pH 7.0). A crude urease sample (FIG. 2) was applied (0.5 mg/ml in PEB, total 8 ml). The column was washed with 15 ml of PB (0.02 M phosphate, 1 mM β-mercaptoethanol, pH 7.0). The column was then washed with 8 ml of each of the following: PB+0.1 M NaCl, PB+0.5 M NaCl, and PB+0.95 M NaCl. The urease was eluted with 8 ml of EB (0.2 M phosphate, 1 mM β-mercaptoethanol, pH 4.6), collecting 1 ml fractions. Fractions were checked by reading OD at 280 nm (FIG. 3) and HPLC (C5 column) analysis. The column was stored in 0.01% $NaN_3$.

B. EXAMPLE 2

Preparation of the Urease-Coil Conjugate

Urease coil conjugate was prepared by dissolving 10 mg of Jack bean Urease in 300 µl of 2 mM phosphate buffer pH 7.2. Then 5 mg of the bifunctional cross-linker Sulfo-MBS was added to the solution and the mixture was slowly stirred for one hour at room temperature. The mixture was then dialyzed against 2 mM phosphate buffer at pH 7.2 to remove excess linker.

K-coil or E-coil with a C-terminal cys linker (1.5 mg) was added to the linker-modified urease solution and slowly mixed for 3 hours at room temperature. The coil urease conjugate was dialyzed against fresh 2 mM phosphate buffer at pH 7.2 overnight to remove unconjugated coil peptide. Dialyzed urease conjugate was lyophilized, then dissolved in 1 mL of 2 mM phosphate buffer pH 7.2 and applied to sephadex G75 column for further purification. The void volume fractions, which contained the coil urease conjugate, were pooled, freeze-dried and stored at 4° C.

The purity of the conjugate and the ratio of the coil to urease in the preparation were determined by amino acid analysis and MALDI mass spectrometry using standard procedures.

C. EXAMPLE 3

Activity Assay of Urease and Urease Conjugate

The enzymatic activity of urease or urease conjugate was carried out in a coupled enzyme reaction with glutamate dehydrogenase (GLDH). The amount of NADH oxidized was determined by measuring the change in absorbance at 340 nm (Kaltwasser, H. and Schlegel, H. G., Anal. Biochem., 16, 132, 1966). The reagents used were: 0.10 M Potassium phosphate buffer, pH 7.6; 1.80 M Urea prepared in phosphate buffer; 0.025 M Adenosine-5'-diphosphate (ADP) (10.7 mg/ml) in buffer; 0.008 M NADH (5 mg/ml) in phosphate buffer; 0.025 M α-Ketoglutarate (3.7 mg/ml) in phosphate buffer; Glutamate dehydrogenase (GLDH) solution, free from ammonium ions; 50 U/ml phosphate buffer prepared fresh prior to assay. Urease solution was prepared by dissolving in phosphate buffer to yield a concentration of 0.1–0.5 U/ml. This solution was prepared fresh prior to assay.

Assay was initiated by adding the following 2.0 mL of Phosphate buffer 2.40 ml, 0.10 ml each of urea, ADP, NADH, GLDH and α-Ketoglutarate in a cuvette. The spectrophotometer was adjusted to 340 nm and 25° C. The cuvette with the added ingredients was placed in the spectrophotometer at 25° C. for 5 minutes to attain temperature equilibration and then establish blank rate, if any, at 340 nm.

To initiate the enzymatic reaction 0.1 ml of the urease solution was added to the cuvette. The changes in the absorbance at 340 nm were recorded for 15 min. Enzyme activity was correlated with a decrease in absorbance at 340 nm per min.

D. EXAMPLE 4

Preparation of Coil Antibody Conjugate

Materials include: (1) Rat Anti-hEGFR IgG2a (Serotec), 200 µg/0.2 ml (i.e. 1 mg/ml); (2) E-coil (N-linker); (3) Sodium m-periodate (Pierce); and (4) Bifunctional crosslinker, KMUH (Pierce).

Functional modification of E-coil was performed by performing the following steps:

a. Dissolve KMUH in DMSO to prepare a 10 mg/ml solution (2.5 mg in 250 µl of DMSO).

b. Dissolve E-coil in PB (~2 mg in 392 µl of 10 mM PB, pH 7.4+4 µl of TCEP, 100 mM stock)

c. Add 1 µl of Tris (2 M) to neutralize the E-coil solution d. Add E-coil solution to the KMUH solution and incubate at R.T. for 2 hr e. Keep solution at 4° C. overnight
f. Next morning, centrifuge at 12000 rpm for 5 min. to remove insoluble precipitate.
g. Remove KMUH and DMSO on a C8 HPLC column (0–20% acetonitrile/$H_2O$ with 0.05% TFA) and collect all peptide fractions (75% acetonitrile).
g. Lyophilize the peptide fractions and check by MS.

The antibody was oxidized by the following steps:
a. For each 2 mg of antibody, weigh 20 mg of periodate in an amber vial.
b. Add 2 ml of PBS, pH 7.2 and 2 ml of stock antibody to the vial (final [antibody] is 0.5 mg/ml) and gently swirl until the periodate powder was dissolved.
c. Incubate at room temp. for 30 min.
d. Remove periodate by dialyzing 3 times vs 100 mM acetate buffer, pH 5.5.

Figure 4:
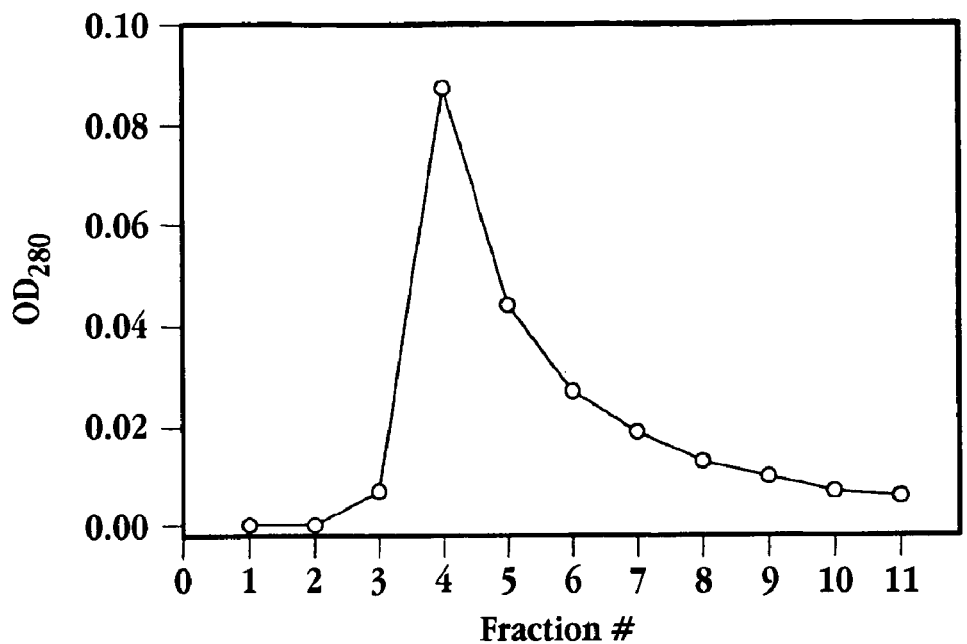
FIG. 4 illustrates the purification of E-coil-αhEGFR IgG conjugate by a protein-G column prepared according to one embodiment of the invention.
Figure 5:
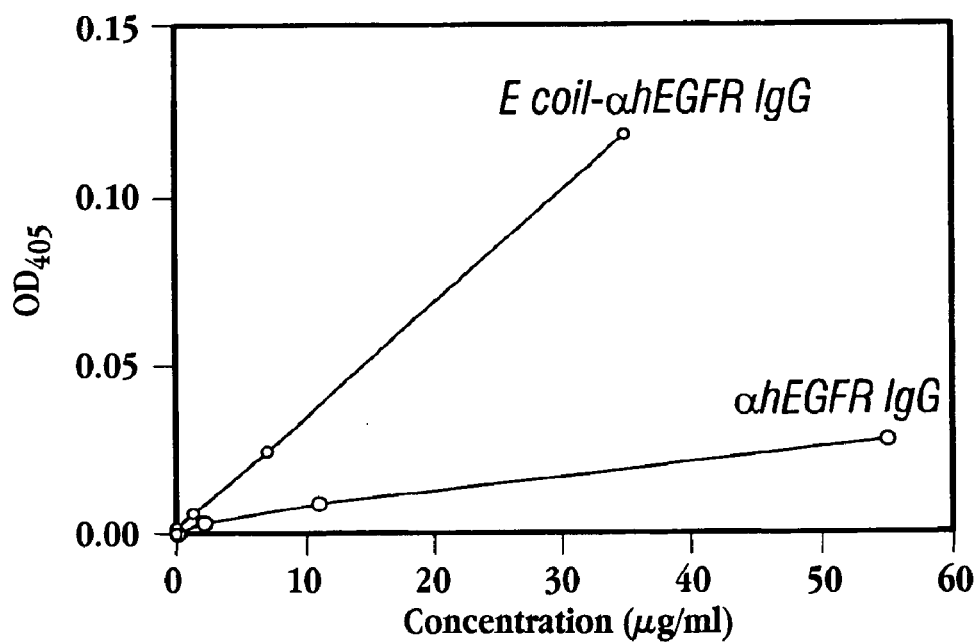
FIG. 5 shows the antibody titer of purified E-coil-αhEGFR IgG conjugate prepared according to one embodiment of the invention as determined by immobilized K-coil ELISA.

Conjugation was performed by the following steps:
a. Concentrate oxidized antibody (~2 mg in 4 ml) using Millipore Ultrafree Filter units (30 k MWc/o).
b. Add 75 µl of the functionalized E-coil solution (4 µg/µl dd$H_2O$) to half of the oxidized antibody solution (containing ~0.75 mg of antibody in acetate buffer, pH 5.5).
c. Incubate at room temp. for 2 hr with shaking.
d. Purify the antibody mixture using a Protein G column (See FIG. 4).
e. Compare and analysis of sample (before and after affinity purification).

E. EXAMPLE 5

Biacore Analysis of Coil Urease Conjugate and Coil Antibody Conjugate

Cysteine containing K-coil peptide or the E-coil peptide was covalent coupled to the Pioneer B1 biosensor chip according to the manufacturer suggested protocol. Briefly, the dextran surface of the sensor chip was first activated with NHS/EDC (15 µl) followed by addition of PDEA (20 µl). K-coil (or E-coil (50 µg/ml) in 10 mM sodium acetate buffer pH 4.3 was injected and allowed to react to give a surface density of approximately 200–400 RU. Remaining activated groups were then blocked by injection (10 µl) of a 50 mM cysteine, 1 M NaCl, 0.1 M formate, pH 4.3 deactivation solution.

Kinetic experiments were performed on a BIAcore3000 instrument at 25° C. Each biosensor run consisted of (1) a 600 s sample injection phase (coil urease or coil antibody), (2) a 600 s dissociation phase, and (3) a 2×15 s regeneration phase (6M guanidine HCl). A flow rate of 5 µl/min was maintained throughout the cycle. PBS was used as a buffer. The SPR signal was recorded in real time with sampling at every 0.5 s and plotted as RU versus time (sensorgram). Each sensorgram obtained was corrected for bulk refractive index changes by subtracting the corresponding sample injection cycle on a blank cell surface.

F. EXAMPLE 6

Animal Studies

Athymic nu/nu female mice with human mammary gland adenocarcinoma xenografts were used for testing. Animals selected were generally 5 to 7 weeks of age, and their body weights at treatment commencement range from approximately 15 to 28 grams.

MCF-cells were used to generate the xenografts. The cells were grown in MEM media supplemented with Penicillin/Streptomycin 50 U/ml, L-glutamine 2 mM, Sodium pyruvate, nonessential amino acids, vitamins, and 10% FBS; The cell incubator was maintained with 5% $CO_2$, 37.5° C., and 80% humidity. The cells were harvested with 0.25% (w/v) trypsin-0.03% (w/v) EDTA solution. Approximately $1\times10^6$ cells in 100 µL was injected subcutaneously to the right flank of each mouse.

Tumor growth was allowed to proceed for about 6–8 days allowing the size of the tumor to reach at least 2–4 mm in diameter. Doses were administered via intratumor injection. The dose volume for each animal was 50 mL. Each solid tumor was injected with the given dose of test article in a "fanning fashion". Tumor volumes were taken by external caliper measurements. Body weights were taken at the start of the trial and at time of sacrifice.

Results, as shown in Table 3 below, show that tumors were not perceptible 24 hours following treatment.

TABLE 3

Successful Treatment of Tumors in Mice

| | Mouse | | | | | |
|---|---|---|---|---|---|---|
| | 1 | 2 | 3 | 4 | 5 | 6 |
| MCF cell injected | $0.8 \times 10^6$ | $0.8 \times 10^6$ | $0.8 \times 10^6$ | $0.8 \times 10^6$ | $1.3 \times 10^6$ | $0.8 \times 10^6$ |
| Tumor size before treatment | 22.5 mm$^3$ | 33.5 mm$^3$ | 15.6 mm$^3$ | 31.1 mm$^3$ | 32.5 mm$^3$ | 8.2 mm$^3$ |
| Urease amount injected | 50 U/50 uL | 50 U/50 uL | 50 U/50 uL | 50 U/50 uL | 40 U/50 uL | 10 U/50 uL |
| Tumor size post injection (24 hours) | not perceptible | not perceptible | Not perceptible | Not perceptible | Not perceptible | Not perceptible |

G. EXAMPLE 7

Urease-Mediated Antitumor Effects in vitro

This example shows that urease is cytotoxic to A549 and MDA-MB-231 cells in culture.

Materials

Urease from *Canavalia ensiformis* (jack beans) was obtained from BioVectra Ltd. (PEI, Canada) and further purified by acid precipitation and ion exchange chromatography to remove the two major contaminants, canavalin and concanavalin A. The purity of the enzyme was >96% as determined by SDS polyacrylamide gel electrophoresis, HPLC and mass spectrometry. One unit of urease is defined as the production of 1 µmole of ammonia per minute at 25° C. and pH 7.6.

Urea, trypsin, phenazine ethosulfate (PES), sodium nitroprusside, sodium hypochlorite solution, phenol, acetohydroxamic acid (AHA), doxorubicin hydrochloride and vinblastine were purchased from Sigma Chemical Co. (St. Louis, Mo.). 3-(4,5-dimethylthiazol-2-yl)-5-(3-carboxymethoxyphenyl)-2-(4-sulfophenyl)-2H-tetrazolium (MTS) was purchased from Promega Corp. (Madison, Wis.). Cell culture medium, serum, and antibiotics were obtained from Invitrogen Life Technologies (ON, Canada). Female athymic nude mice were supplied by Charles River Laboratories (Wilmington, Mass.). Buffers used in the experiments: Dulbecco's phosphate-buffered saline (D-PBS) and modified Krebs Ringer buffer (KRB) containing NaCl (98.3 mM), KCl (4.73 mM), $KH_2PO_4$ (1.19 mM), $MgSO_4$ (1.19 mM), $NaHCO_3$ (3.57 mM), D-Glucose (11.7 mM), $Na_2HPO_4$ (11.1 mM) and $NaH_2PO_4$ (2.77 mM) at pH 7.2 or 6.8.

Cell Culture and Viability Assay

Human breast cancer cell lines (MDA-MB-231 and MCF-7) and lung cancer cell line (A549) were purchased from the American Type Culture Collection (Manassas, Va.). Cells were grown in DMEM/F12 (MDA-MB-231 and A549) or MEM (MCF-7) containing 10% fetal bovine serum and 50 U/ml penicillin and 50 µg/ml streptomycin at 37° C. in a humidified incubator with 5% $CO_2$.

Colorimetric MTS assay was employed to determine cell viability. MTS and PES were dissolved in D-PBS and filtered to prepare 2 and 1 mg/ml stock solutions, respectively. After the cells were treated with test articles, the medium in the plate was replaced with 100 µl/well of plain culture medium, followed by the addition of 20 µl/well of MTS mix (MTS: PES at 20:1, vol/vol). The plate was incubated for 1–2 hours at 37° C. in a humidified, 5% $CO_2$ atmosphere. The absorbance of soluble formazan produced by cellular reduction of MTS was measured at 490 nm with reference at 630 nm using an ELx808IU Microplate Reader (Bio-tek Instruments Inc., Winooski, Vt.).

In vitro Cytotoxicity of Urease

A549 cells ($1.0 \times 10^5$ cells/ml) or MDA-MB-231 cells ($1.5 \times 10^5$ cells/ml) were seeded into 96-well tissue culture plates (Becton Dickinson Labware, N.J.) by transferring aliquot of 100 µl of the cell suspension to each well. The plate was incubated at 37° C. overnight. After incubation, the medium in the wells was removed using a multichannel pipette. Urease and urea at various dilutions were prepared in pre-warmed KRB, pH 7.2 and 50 µl of each was added to corresponding wells. After incubation for two hours at 37° C., buffer from each replicate was pooled and subjected to pH measurement and total ammonium determination as described in Example 8. MTS cell viability assay was then performed on the plate.

Results

Figure 6A:
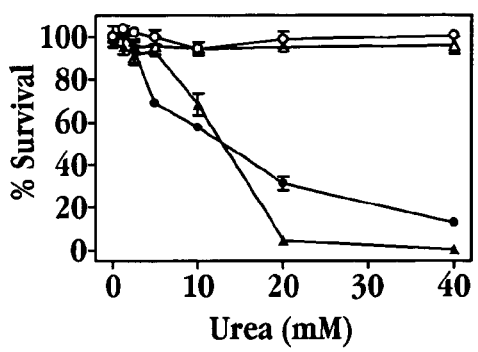
FIG. 6A is a graph showing a dose-response curve of urea on the viability of A549 (▲) and MDA-MB-231 (●) cells. Cells were incubated in 0–40 mM urea, treated with 2 U/ml of urease and incubated at 37° C. for 2 hours as more fully described in Example 7. Viability of the treated cells began to drop as the urea level increased. Urea alone has no effects on A549 (Δ) and MDA-MB-231 (○) controls.
Figure 6C:
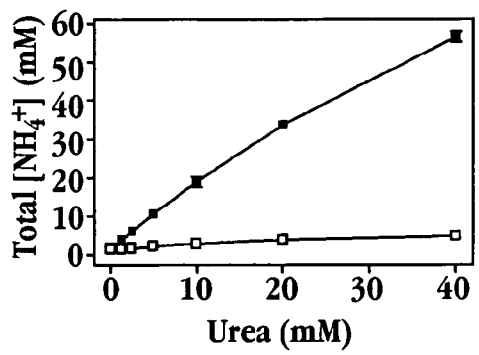
FIG. 6C is a graph showing total ammonium ion as a function of urea treatment in pooled incubation buffer collected from A549 cells treated with urease as described for FIG. 6A and as more fully described in Example 8. Hydrolysis of urea by urease (■) caused an increase in ammonium content as compared to the control (□). Values are means±S.D. of 4 replicates from 3 experiments.
Figure 6B:
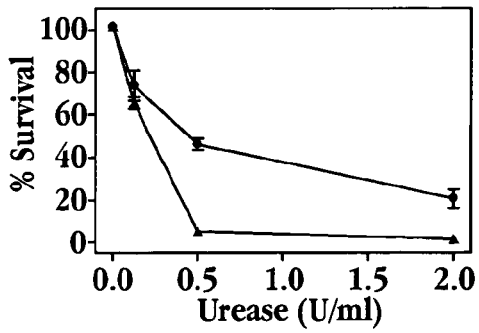
FIG. 6B is a graph showing a dose-response curve of urease on the viability of A549 (▲) and MDA-MB-231 (●) cells. Cells were incubated in 20 mM urea and treated with 2 U/ml of urease for 2 hours as described in Example 7. A549 (▲) were more susceptible to urease than MDA-MB-231 (●) cells.

Human tumor cell lines A549 and MDA-MB-231 were susceptible to the enzymatic activity of jack bean urease. The survival rate of both cell lines decreased as the cells were treated with 2 U/ml of urease for 2 hours with an increasing amount of urea in the medium (FIG. 6A). Urea alone (up to 40 mM as tested) was not toxic to the cells during the 2-hour incubation period. In the presence of 2 U/ml of urease, the $IC_{50}$ of urea were found to be 13 mM for both cell lines (FIG. 6A). Furthermore, the cytotoxic effects were also dependent on the availability of urease. With fixed urea concentration at 20 mM in the medium, the $IC_{50}$ of urease were found to be 0.22 and 0.45 U/ml, respectively, for A549 and MDA-MB231 cells (FIG. 6B). Sufficient amounts of ammonia produced by urease therefore mediate cell death on both human lung and breast cell lines described herein. Urease can therefore be used alone through the direct cytotoxicity of ammonia.

It was found herein that significant amounts of canavalin and concanavalin A contaminants were present in a commercial source of crystalline urease as detected by HPLC and mass spectrometry. These contaminants were able to increase in vitro cytotoxicity of the enzyme (unreported observation).

H. EXAMPLE 8

Effect of Urease on pH and Ammonium Concentration of Culture Medium of A549 Cells This example shows that urease increases the total ammonium content and the pH of culture medium from A549 cells in culture.

Methods

The total ammonium present in the incubation buffer obtained from plates utilized in the in vitro cytotoxicity studies in Example 7 was determined by Berthelot's Indophenol reaction (Chaney, A. L. and Marback, E. P. Clin. Chem. 8:130–132 (1962)). In brief, fresh phenol solution (Solution A) was prepared by dissolving 165 mg of phenol and 132 mg of NaOH pellets in 10 ml of water, and then 66 µl of sodium nitroprusside solution (10 mg/ml) was added. Fresh Solution B was prepared by adding 80 µl of sodium hypochlorite solution (10–13% chlorine) to 10 ml of water. Urease activity in the pooled sample was quenched by adding 50 µl of 1 N HCl to 100 µl of sample. The acidified samples were then diluted 200 times and transferred to a 96-well microplate at 100 µl/well, followed by 50 µl of Solution A and 50 µl of Solution B. After incubation at 37° C. for 15 min, the plate was read at 630 nm using the microplate reader. The amount of ammonium ions present in the sample was determined from the $NH_4Cl$ standard curve. Cell culture and viability assays were performed as described in Example 7.

Results

Figure 6D:
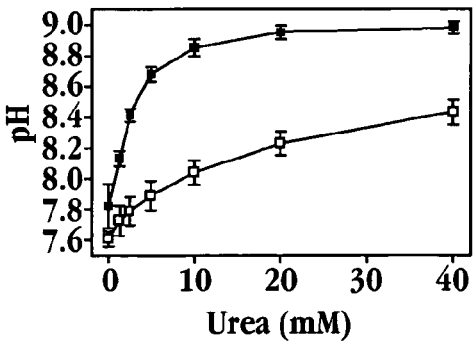
FIG. 6D is a graph of pH as a function of urea treatment in pooled incubation buffer collected from A549 cells treated with urease as described for FIG. 6A and as more fully described in Example 8. Hydrolysis of urea by urease (■) caused an increase in pH as compared to the control (□). Values are means±S.D. of 4 replicates from 3 experiments.

The antitumor effects of urease observed in Example 7 were exerted through the hydrolysis of urea into ammonia (FIG. 6C) with a corresponding elevation of pH (FIG. 6D) due to protonation of ammonia in aqueous medium. FIGS. 6C and 6D were the total ammonium and pH measured in the reaction buffer collected from experiments of FIG. 6A. It was found that urease cytotoxicity (FIG. 6A) correlated well with a corresponding increase of ammonium content and pH in the incubation buffer (FIGS. 6C and 6D). The rise in pH of the control as shown in FIG. 6D was probably due to autolysis of urea in aqueous medium resulted in the generation of a total of 3 to 5 mM of ammonium. However, separate experiments have shown that pH alone was insufficient to cause any significant cytotoxicity on the two cell lines during a two-hour incubation window (data not shown). Therefore, it was the level of ammonium, or more specifically, availability of free ammonia, that mediated the rapid cell killing effects. An augmented pH in turn increases the availability of free ammonia to the cells according to the following equation:

$$pH = pK + \log\frac{[NH_3]}{[NH_4^+]}, \text{ where } pK = 9.3 \text{ at } 37°C. \tag{2}$$

I. EXAMPLE 9

Effects of Acetohydroxamic Acid on Urease Cytotoxicity In Vitro and the Ammonium Content of Culture Media This example shows that acetohydroxamic acid decreases the total ammonium content of cell culture medium and protects tumor cells in the culture medium from urease cytotoxicity. Cells were cultured and viability was determined as described in Example 7. The ammonium content of culture medium was determined as described in Example 8.

Results

Figure 7A:
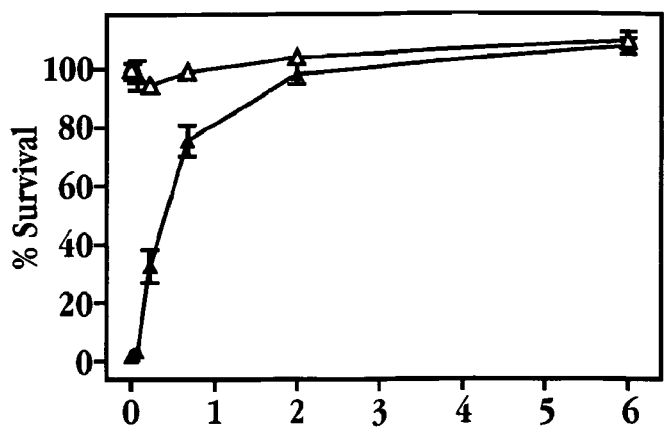
FIGS. 7A–7F are graphs depicting the protective effects of acetohydroxamic acid (AHA) on urease cytotoxicity as described in Example 9. (A) A549 cells (▲) and (B) MDA-MB-231 cells (●) treated with 2 U/ml of urease were protected from the cytotoxic effects by addition of acetohydroxamic acid to the incubation buffer. AHA alone at concentrations up to 6 mM was not toxic to both cell lines (no urease controls: Δ, A549; ○, MDA-MB-231). Complete protection was observed at dose ≧2 mM. (C) AHA inhibited ammonium production by urease (■), which corresponds to an increase in survival rate of both cell lines as shown in (A) and (B). Higher amount of AHA (6 mM) can reduce the ammonium level close to that of control (□). Values are means±S.D. of 4 replicates from 3 experiments. (D) AHA inhibited ammonium production by urease at indicated urea concentrations; (E) A549 cells; or MDA-MB-231 cells incubated in the indicated amounts of urea and treated with 2 U/ml urease were protected from the cytotoxic effects of urease by addition of acetohydroxamic acid to the incubation buffer.
Figure 7B:
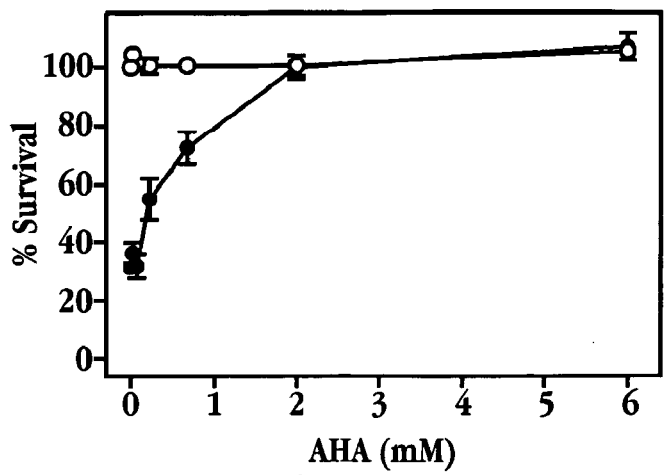
Figure 7C:
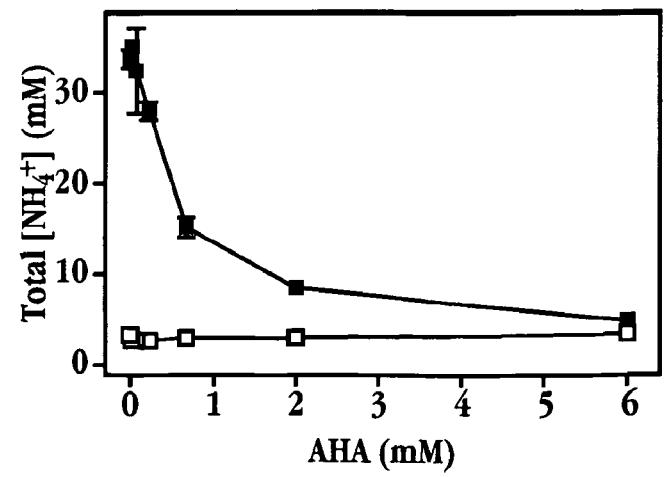
Figure 7D:
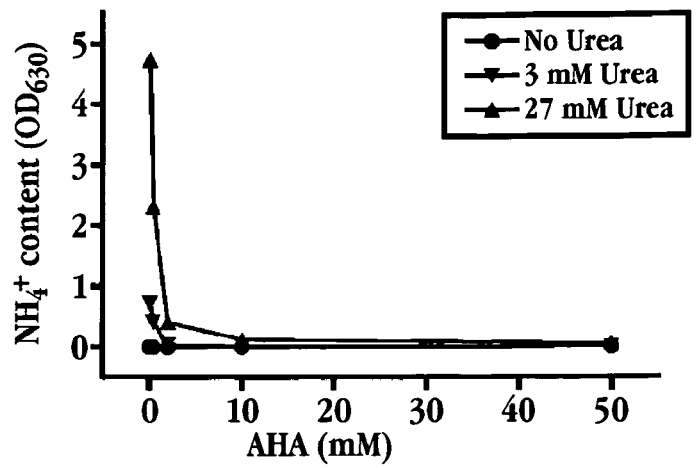
Figure 7E:
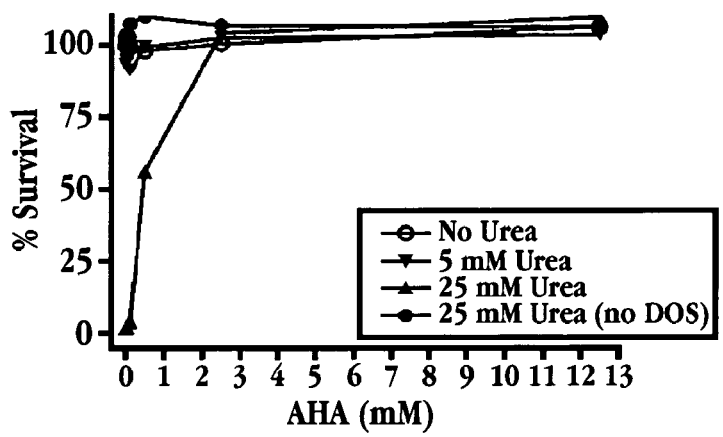
Figure 7F:
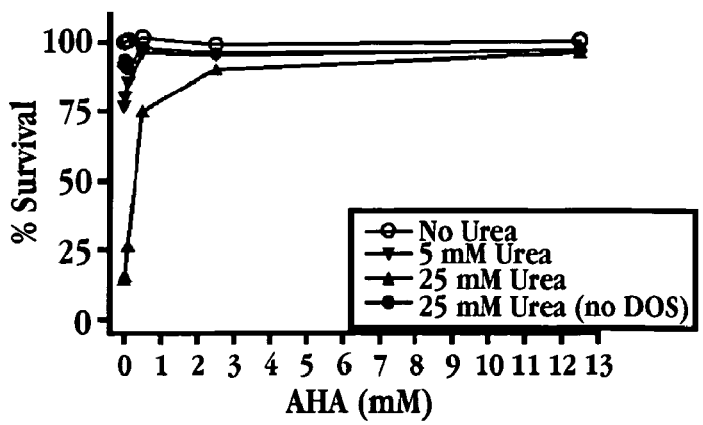
Figure 8A:
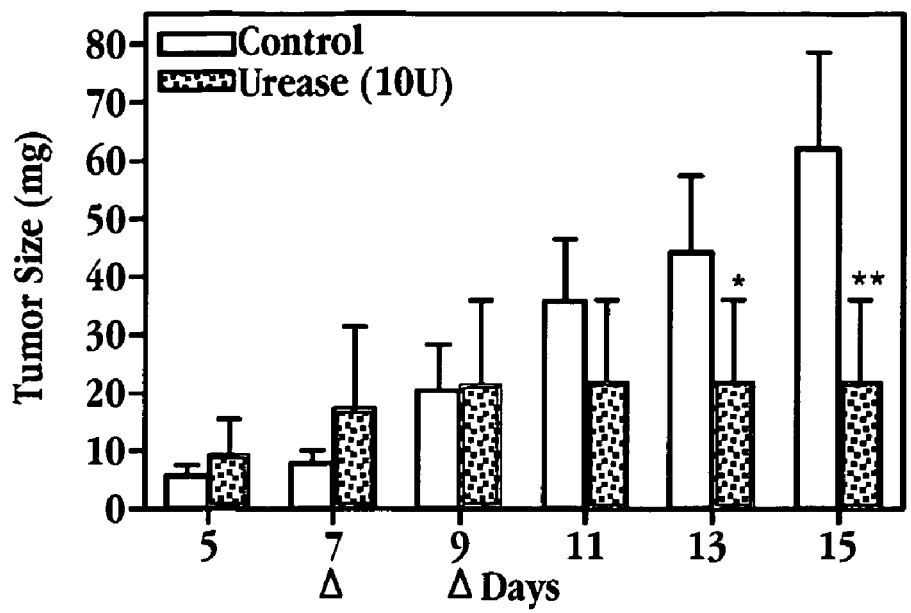
FIGS. 8A–8B are graphs which depict the growth inhibitor effects of urease on tumor cell line xenografts as described in Example 10. (A) urease inhibits the growth of established MCF-7 xenografts. The breast tumor stopped to grow after the second injection of high-dose of urease (10 U/injection, solid bars) on day 9 as compared to the controls (open bars). Time of intratumoral injections are indicated by Δ below the x-axis. (B) effects of multiple low-dose (1 U/injection, hatched bars) and medium-dose (4 U/injection, solid bars) injections of urease on established A549 xenografts. Intratumoral injections were performed on days 5, 7, 9, 11 and 13 (Δ). Delay of tumor growth was observed from days 17 onwards as compared to the controls (open bars). Significance was determined using the two-tailed unpaired Student's t test: *P<0.05 and **P<0.005.
Figure 8B:
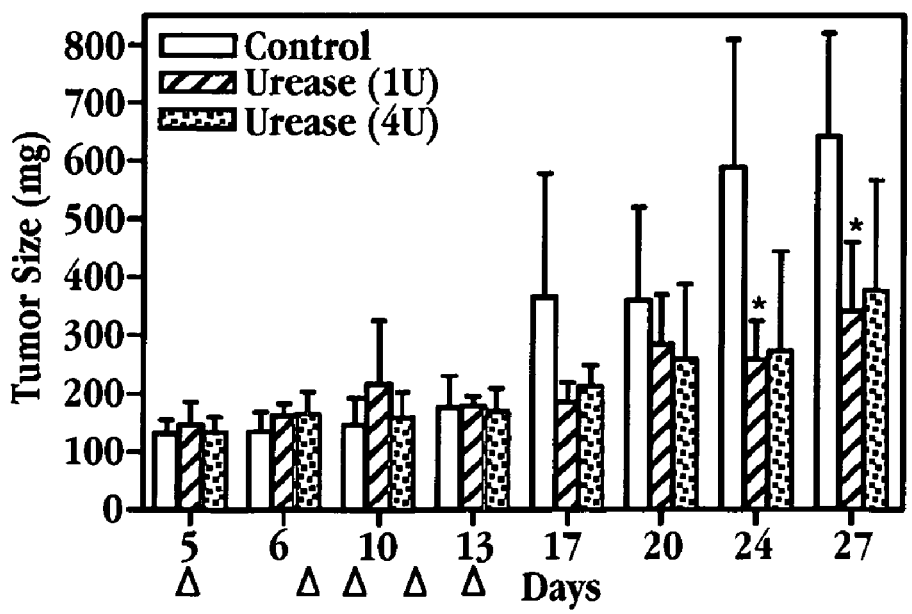

Acetohydroxamic acid (AHA) is a potent reversible inhibitor of urease and is commercially available for the treatment of chronic urea-splitting urinary infection. When AHA was added to the culture buffer containing urease, it effectively inhibited the enzymatic activity of urease (FIG. 7C) and restored the survival rate of A549 (FIG. 7A) and MDA-MB-231 (FIG. 7B) cells to normal level at dose $\geq 2$ mM. This result suggested that the cytotoxicity of urease is solely due to its enzymatic activity. Similar results are shown in FIG. 8A–8C at different levels of urea. Two millimolar AHA can reduce ammonium production by DOS47 (urease) at 27 mM urea to a level similar to that of 3 mM urea, and thus protects cells from being killed (FIG. 7D). It is estimated that AHA at 0.8 mM can reduce the ammonium production by half (FIG. 7D). AHA at 2.5 mM can almost completely reverse the cytotoxic effects of DOS47 in KR-II buffer containing 25 mM urea during a 2 hour incubation period for both A549 and MB-231 cells (FIGS. 8E and 8F). AHA is not toxic to both cell lines at concentrations as high as 12.5 mm (FIGS. 7E and F). In comparing FIGS. 6 and 8, it can be seen that short term in vitro urease treatment required much higher levels of urea than that of longer term in vivo treatment.

J. EXAMPLE 10

Anti-Cancer Effects of Urease in vivo

This example shows that MCF-7 and A549 xenografts from mice are susceptible to intratumoral injections of urease.

Methods

A549 xenografts: Female athymic nude mice (7–9 weeks old) were injected subcutaneously in the right lateral thorax with $5 \times 10^6$ human A549 lung cancer cells. When tumors reached 100–200 mg, the tumor-bearing animals were randomly selected and sorted into four groups. Group 1 contained ten untreated control mice. Group 2 contained ten positive control mice treated with the reference chemotherapeutic agent Cisplatin. Groups 3 and 4 contained 15 mice each that received one of two different concentrations of urease (1 U or 4 U per injection). Each animal received five doses of injection scheduled at 48 hours between treatments (q2d×5). Urease was administered intratumorally, whereas cisplatin was administered via an intravenous tail vein injection.

Twenty-four hours after the fifth urease administration, five mice from each group were sent for necropsy and tumor collection. In addition, five mice from Groups 2–4 were euthanized and tumors were collected, dissociated, and cultured for viability testing. The remaining five animals from each group continued on study until study termination. Tumor size was recorded using calibrated hand-held Vernier calipers. Throughout the study, the length (L) and width (W) of any tumors that developed were measured in millimeters. The tumor weight in mg was calculated using the formula: (L×W2)/2. Individual animal weights were taken twice weekly. The experimental protocol was covered under Charles River Laboratories Institutional Animal Care and Use Committee (IACUC).

MCF-7 xenograft: Female athymic nude mice were injected subcutaneously with $1.8 \times 10^6$ MCF-7 breast tumor cells. When tumor size reached approximately 9 mg, eight mice were injected intratumorally with two doses of urease (10 U/injection) at 48 hours interval (q2d). Five mice were treated with saline as control. The condition of all animals and tumor size were monitored 24 hours after inoculation and then every other day. Animal care was in accordance with the guidelines of the Canadian Council on Animal Care (CCAC). At the end of the observation period, tumors were excised and prepared for histology analyses.

Results

Both MCF-7 and A549 xenografts were susceptible to intratumoral injections of urease. Growth of MCF-7 was completely stopped after the second injection of 10 U of urease (FIG. 8A). Histological analysis of tumors excised from the treated mice showed that the tumor mass was dead and could not re-grow in culture medium.

In the case of A549 xenografts, delay in tumor growth was observed in mice treated with 5 injections of low dose (1 U) or medium dose (4 U) of urease (FIG. 8B). Growth regressions of the urease-treated groups were similar to that of the positive control group treated with 6 mg/kg Cisplatin (data not shown). Tumor tissue slices showed significant necrotic area compared to the control. However, cell viability was not affected (>82%) in dissociated tumors taken from mice treated with urease. There were no significant differences in body weight of the treatment and control groups in both xenograft studies.

K. EXAMPLE 11

In vitro Anti-Cancer Effects of Urease in Combination with Selected Anti-Neoplastic Drugs This example shows that urease enhances the anti-cancer effects of doxorubicin, vinblastine, fluorouracil, and mitoxantrone.

Methods

Combined Drug Assays

A549 and MDA-MB-231 plates were prepared as described in Example 7. Urease, urea and the 4 weak-base anticancer drugs, doxorubicin, vinblastine, fluorouracil and mitoxantrone were prepared in pre-warmed KRB, pH 6.8. After the medium in the plate was removed, 50 μl of urease, urea and drug solutions were added subsequently into corresponding wells. The final concentrations of doxorubicin, vinblastine, fluorouracil and mitoxantrone were 50 μM, 100 μM, 13.3 mM and 5 μM, respectively. After 2-hour incubation at 37° C., cell viability assays were performed as described in Example 7 and the buffer pH was measured.

Results

Figure 9A:
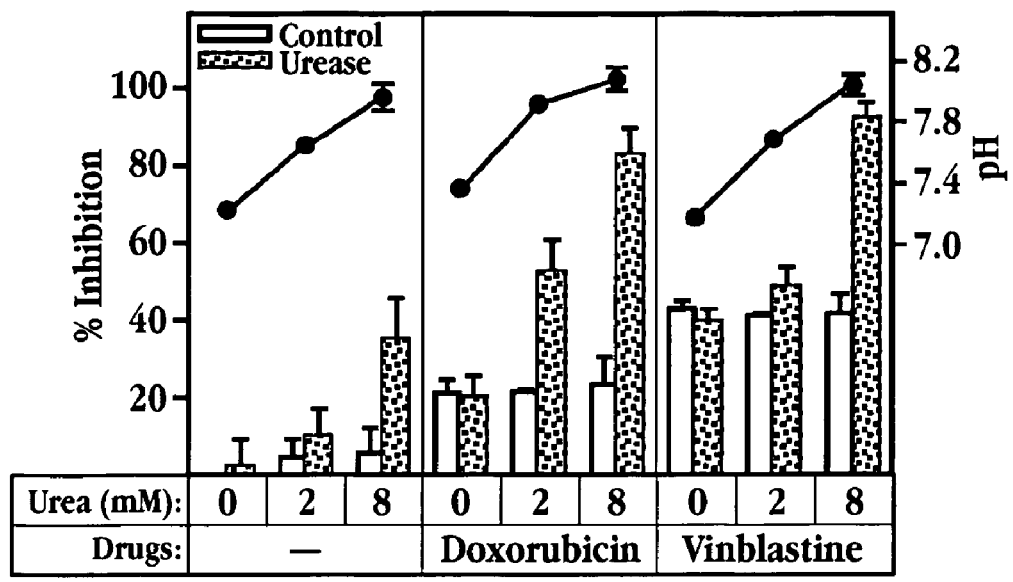
FIGS. 9A–9B are graphs depicting the effects of urease on the cytotoxicity of weakly basic anticancer drugs as described in Example 11. (A) lung tumor A549 and (B) breast tumor MDA-MB-231 incubated in 0, 2 or 8 mM urea, were treated with 2 U/ml of urease, and either 50 μM of doxorubicin or 100 μM of vinblastine at pH 6.8 overnight. The antitumor efficacies of the two compounds were enhanced at the presence of urease (solid bars) and urea as compared to the control (open bars). The solid circle (●)
Figure 9B:
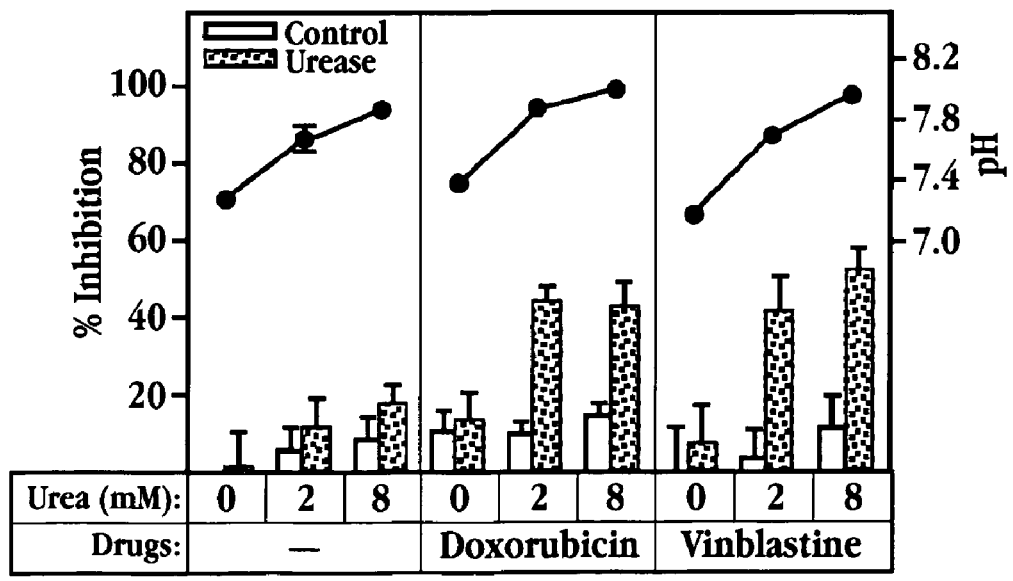

Krebs Ringer buffer at pH 6.8 was used to mimic the acidic extracellular environment of solid tumor. At this incubation condition, the pH raised by the urease activity was lower than what was observed in FIG. 6D. However, the pH increase was sufficient to enhance the antitumor efficacy of the two weak-base anticancer drugs tested. At low urea level (2 mM), urease significantly enhanced the antitumor activity of doxorubicin on A549 (FIG. 9A) and MDA-MB-231 cells (FIG. 9B), as well as that of vinblastine on MDA-MB-231 cells (FIG. 9B). When urea level was increased to 8 mM, urease enhanced the activity of both drugs on both cell lines (FIG. 9).

The antitumor efficacy of another weak-base anticancer drug, mitoxantrone, was also significantly enhanced by urease when used to treat MDA-MB-231 cells (FIG. 10B) but not on A549 cells (FIG. 10A). Interestingly, the activity of fluorouracil, which is not a weak-base drug, was also enhanced by urease on A549 cells (FIG. 10A).

Although the invention has been described with respect to particular embodiments, it will be apparent to those skilled in the art that various changes.

Although the invention has been described with respect to particular embodiments, it will be apparent to those skilled in the art that various changes and modifications can be made without departing from the invention.

It is claimed:

1. In a method of treating cancer cells whose extracellular environment contains 1–8 mM urea, by exposing said cells to a weakly basic anti-cancer compound which is effective in inhibiting the growth of said cells, an improvement comprising
   (a) exposing the cells to a composition containing a urease enzyme, and
   (b) by step (a), reducing the amount of said anti-cancer compound required to produce a given extent of inhibition in the growth of said cells, when the cells are exposed to the anti-cancer agent.

2. The improvement of claim 1, wherein said exposing is effective to raise the pH of the extracellular environment of the cancer cells by at least 0.1 pH unit.

3. The improvement of claim 2, wherein said anti-cancer compound is selected from the group consisting of doxorubicin, daunorubicin, mitoxantrone, epirubicin, mitomycin, bleomycin, a vinca alkaloid, an alkylating agent, or an antineoplastic purine and pyrimidine derivative.

4. The improvement of claim 2, wherein the amount of said anti-cancer compound required to achieve the same extent of cell-growth inhibition is between about 2-fold and 5-fold less than in the absence of step (a).

5. The improvement of claim 2, wherein said composition includes a targeting moiety attached to said urease enzyme and selected from the group consisting of an antibody directed against a tumor antigen, an anti-hCG antibody, and a ligand capable of binding specifically to a cancer-cell surface receptor.

6. The improvement of claim 5, wherein said targeting moiety is a single-chain antibody.

7. The improvement of claim 2, in a method for treating a cancer in a mammalian subject, by administration of such anti-cancer compound to the subject, wherein step (a) includes administering to the subject, a urease composition effective to localize at the site of the cancer in the subject.

8. The improvement of claim 7, wherein said urease composition is administered intravenously in an amount of between 25 and 2000 pmoles urease enzyme/kg subject body weight, at least 24 hours prior to administration of the anti-cancer compound.

9. The improvement of claim 8, wherein said urease composition is administered by IV drip and the composition includes a urease inhibitor selected from the group consisting of a hydroxamic acid derivative and other urea analogs, in an amount effective inhibit the activity of the urease enzyme at the initial concentration of the urease composition.

10. The improvement of claim 7, for use in treating a solid tumor, wherein said urease composition is administered directly in the tumor in an amount effective to raise the pH total of the extracellular fluid of said tumor, as evidenced by detectable change in a pH indicator present in the tumor extracellular fluid.

11. A method of treating a cancer that is responsive to a selected weakly basic anti-tumor compound in mammalian subject, comprising:
   administering to the subject, such weakly basic anti-cancer compound and an amount of a urease enzyme composition sufficient to potentiate the therapeutic effect of the compound with respect to the therapeutic effect obtained in the absence of said urease composition administration.

12. The method of claim 11, which includes administering said urease composition at least 24 hours prior to administering the anti-cancer compound.

13. The method of claim 11, which includes co-administering the anti-cancer compound and the urease composition.

14. The method of claim 11, wherein urease composition is administered in an amount effective to raise the pH of the extracellular environment of the cancer cells by at least 0.1 pH unit.

15. The method of claim 11, wherein administration of the urease composition is effective to reduce the amount of said anti-cancer compound required to achieve the same extent of cell-growth inhibition by a factor of between 2 and 5.

16. The method of claim 11, wherein said anti-cancer compound is selected from the group consisting of doxorubicin, daunorubicin, mitoxantrone, epirubicin, mitomycin, bleomycin, a vinca alkaloid, an alkylating agent, or an antineoplastic purine or pyrimidine derivative.

17. The method of claim 11, wherein said urease composition includes a targeting moiety attached to said urease and selected from the group consisting of an antibody directed against a tumor antigen, an anti-hCG antibody, and a ligand capable of binding specifically to an cancer-cell surface receptor.

18. The method of claim 11, wherein said urease composition is administered by IV drip in an amount of between 25 and 2000 pmoles urease enzyme/kg subject body weight, and the composition includes a urease inhibitor selected from the group consisting of a hydroxamic acid derivative and other urea analogs, in an amount effective to inhibit the activity of the urease enzyme at the initial concentration of the urease composition.

19. In a subject having a solid tumor a method of enhancing the therapeutic efficacy of a weakly basic anti-tumor compound whose effectiveness is reduced by a higher intracellular/lower extracellular pH gradient in a solid tumor, comprising administering to the subject receiving said anti-tumor compound, an amount of urease effective to reduce or reverse the higher intracellular/lower extracellular pH gradient in a solid tumor.

20. The method of claim 19, wherein said anti-tumor compound is selected from the group consisting of doxorubicin, dauorubicin, mitoxanthrone, epirubicin, mitomycin, bleomycin, vinca alkaloids, alkylating agents and antineoplastic purine and pyrimidine derivatives.

21. The method of claim 19, wherein said administering is effective to raise the extracellular fluid of the tumor of at least pH 7.2.

22. The method of claim 19, wherein said administering includes injecting urease directly into the subject's tumor.

23. The method of claim 19, wherein said urease is administered parenterally other than by direct injection in a composition that includes a chemical entity effective to enhance the delivery of the enzyme to a solid tumor.

24. The method of claim 20, wherein the vinca alkaloid is selected from the group consisting of vinblastine and vincristine.

25. The method of claim 20, wherein the alkylating agent is selected from the group consisting of cyclophosphamide and mechlorethamine hydrochloride.

* * * * *